United States Patent [19]
Posner et al.

[11] Patent Number: 6,136,847
[45] Date of Patent: Oct. 24, 2000

[54] WATER-SOLUBLE TRIOXANES AS POTENT AND SAFE ANTIMALARIAL AGENTS

[75] Inventors: Gary H. Posner; Michael H. Parker; Mikhail Krasavin; Theresa A. Shapiro, all of Baltimore, Md.

[73] Assignee: Johns Hopkins University, Baltimore, Md.

[21] Appl. No.: 09/287,353

[22] Filed: Apr. 7, 1999

Related U.S. Application Data

[63] Continuation-in-part of application No. 08/758,661, Dec. 2, 1996, Pat. No. 5,932,591.
[51] Int. Cl.[7] ..................... A61K 31/335; A61K 31/357; A61P 33/06; C07D 323/06
[52] U.S. Cl. .................... 514/450; 514/730; 514/784; 514/311; 514/314; 514/422; 514/428; 514/444; 514/461; 546/152; 546/174; 548/517; 548/526; 549/60; 549/368; 549/472; 549/473
[58] Field of Search .............................. 549/368; 514/450

[56] References Cited

FOREIGN PATENT DOCUMENTS

WO 92/02217  2/1992  WIPO .

OTHER PUBLICATIONS

Posner et al., "Synthesis and antimalarial activities of structurally simplified 1,2,4–trioxanes related to artemisinin," Heteroat. Chem., 6(2), pp. 105–116 (Abstract), 1995.
Posner et al., "Evidence for the Importance of High Valent Fe=O and of a Diketone in the Molecular Mechanism of Action of Antimalarial Trioxane Analogs of Artemisinin," J.Am.Chem.Soc., vol. 118, pp. 3537–3538, Apr. 10, 1996.

*Primary Examiner*—Joseph McKane
*Assistant Examiner*—Jane C. Oswecki
*Attorney, Agent, or Firm*—Pillsbury Madison & Sutro LLP

[57] ABSTRACT

Biologically-active, water soluble, 3-substituted trioxanes of the formula

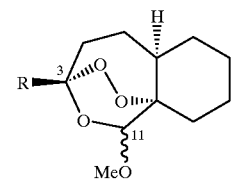

wherein R represents a COOH— substituted aryl group, a substituted or unsubstituted heteroaryl group or an alkyl group, and $C_{12}$-(p-carboxy)benzyloxy trioxanes of formula

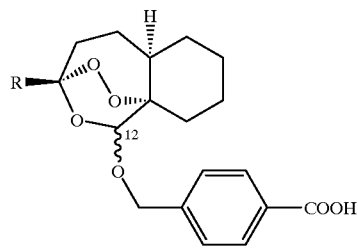

wherein R represents a substituted or unsubstituted alkyl, alkenyl, aryl or heteroaryl group and methods for their use as antiparasitic agents, particularly for the treatment of malaria.

15 Claims, No Drawings

WATER-SOLUBLE TRIOXANES AS POTENT AND SAFE ANTIMALARIAL AGENTS

This application is a continuation-in-part of U.S. application Ser. No. 08/758,661, filed Dec. 2, 1996, now U.S. Pat. No. 5,932,591.

The invention described and claimed herein was made in part under Grant No. AI 34885 from the National Institutes of Health. The U.S. Government has certain rights in the invention.

BACKGROUND OF THE INVENTION

1. Field of the Invention

The present invention relates to novel biologically-active water soluble 3-substituted trioxanes and to their use as antiparasitic agents, particularly in malaria treatment.

2. Description of the Related Art

The trioxane drug artemisinin is an active anti-malarial constituent of the herb *Artemisia annua* L., Compositae. The herb has been known in China for almost 2000 years. Artemisinin was first isolated in 1972 and shown to be a sesquiterpene lactone with a peroxide moiety (1). The molecular structure was first reported in 1983 (2) and is shown in the following formula:

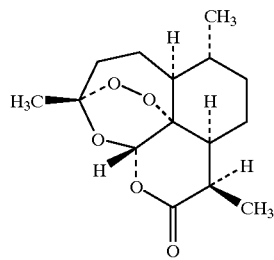

Several investigators have reported on the anti-malarial activity of artemisinin (3–5), and reviews of the chemistry, pharmacology and clinical applications of artemisinin have been published (6–8).

In addition to artemisinin, a number of related synthetic organic endoperoxides have been developed which have antimalarial activity. Saturated and unsaturated bicyclic endoperoxide compounds with antiparasitic/antimalarial activity are disclosed in U.S. Pat. Nos. 5,672,624 and 5,817,692 (both of which are hereby incorporated herein by reference), and 1,2,4 trioxane analogs of Artemisinin have been described (9). Avery et al. (10) described 3-substituted Artemisinin analogs, and noted that substitution with branched hydrocarbons lowered antimalarial potency appreciably.

A number of useful water-insoluble 3-substituted trioxanes were disclosed in prior U.S. application Ser. No. 08/758,661 (hereby incorporated herein by reference). Although effective, the use of these compounds for oral or IV administration is somewhat limited by their poor solubility in water.

Artelinic acid is a semisynthetic water soluble derivative of artemisinin of the formula

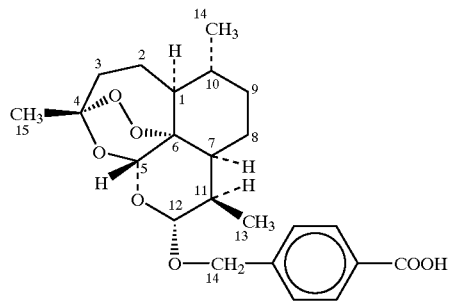

which has also been found useful for the treatment of malaria. One disadvantage of this compound is that its production requires significant quantities of the crop *Artemisia annua*, which is used as starting material for the synthesis.

Biological evaluation of these compounds indicates that a number of them are effective antiparasitic agents. However, parasitic infections, particularly malaria, remain a serious and widespread public health problem, and concern exists about possible side effects of compounds developed to date. For example, neurotoxicity has been seen in rats which were administered high doses of artemether and in mouse neuroblastoma cells treated with dihydroartemesisin (11). For this reason, a need remains for the development of improved therapeutic agents for prevention and treatment of malaria.

SUMMARY OF THE INVENTION

It is an object of the present invention to provide compounds and methods for treating parasitic infections such as malaria and cerebral toxoplasmic encephalitis. To accomplish this object, the invention provides 3-substituted trioxanes of the formula

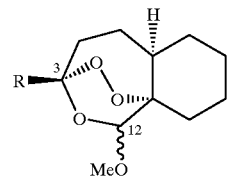

wherein R represents a substituted or unsubstituted alkyl or aryl group of 1–20, preferably 1–12, carbon atoms. It will be appreciated by one of skill in the art that this structure contains an asymmetric center at position 12 and that the MeO group in position 12 may be in either an α or β orientation.

The term "aryl" according to the invention, is intended to mean a compound or substituent having at least one aromatic ring, and is particularly intended to include phenyl, biphenyl, and heterocyclic aromatic rings of 5–6 atoms or bicyclic rings of up to 10 atoms which have at least one nitrogen, sulphur or oxygen atom. The term "alkyl" according to the invention, is intended to mean a saturated aliphatic hydrocarbon group, particularly a straight or branched carbon chain of 1–12 carbon atoms. The term "alkenyl" according to the invention, is intended to mean an unsaturated aliphatic hydrocarbon group, particularly a straight or branched carbon chain of 1–12 carbon atoms.

In one preferred embodiment of the invention, R represents an aryl or functionalized aryl which is a substituted or unsubstituted phenyl or biphenyl group. Particularly preferred in this regard are substituents which are unsubstituted or have substitutions in the para position, for example Ph, p-PhPh, p-FPh, p-F-o-MePh, p-MeOPh, p-(HOCH$_2$)Ph, p-formyl-Ph, p-diethylaminomethyl-Ph, p-CF$_3$Ph and p-HO$_3$SPh. Another particularly preferred substituent is m,m'-(HOCH$_2$)$_2$Ph. Preferred embodiments of the invention are also considered to include combinations of two or more potentiating groups, e.g. wherein the phenyl group is substituted with two or more of substituents F—, MeO—, HOCH$_2$—, and so forth.

In another preferred embodiment of the invention, R represents a heteroaryl or functionalized heteroaryl group, for example a furyl, thienyl, or quinolyl group. Particularly preferred substituents in this regard include 2-furyl, 2-thienyl, and 3-quinolyl.

In another embodiment of the invention, R represents a substituted or unsubstituted alkyl or alkenyl group, particularly a mono- or polyfluoroalkyl group. Examples of substituents of this embodiment are fluoromethyl, ethyl, vinyl, (CH$_3$)$_2$CHCH$_2$CH$_2$, trifluoromethyl, and (3,3,3)-trifluoropropyl.

Two particularly preferred embodiments of the invention are the MHP-34 trioxanes, MHP-34a and MHP-34b, represented by the formulas:

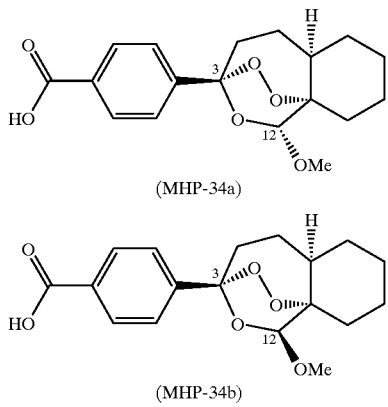

(MHP-34a)

(MHP-34b)

These compounds have the following advantages:
1. They have improved water solubility. The water solubility of MHP-34a and -34b is about 0.09M and 0.06M, respectively, in pH 7.4 aqueous solution, compared to ~0.002M for artelinic acid.
2. They have high oral efficacy in mammals. MHP-34a is orally active in curing mice infected with P. berghei malaria (ED$_{90}$=46 mg/kg/day×4), more orally efficacious than artelinic acid (SD$_{50}$=56 mg/kg/day×4).
3. They have high efficacy via IV administration to mammals.
   Both MHP-34a and -34b cure mice infected with P. berghei malaria (ED$_{90}$=60 mg/kg/day×4).
4. They are nontoxic in therapeutic dose range. IV administration of MPH-34a daily for 14 days to rats caused no hemolysis of erythrocytes. In the same dosing scheme, artelinic acid caused time-dependent hemolysis even at a dose four-fold less than that of MHP-34a.
5. Their synthesis is economical. Both MHP-34a and -34b can be synthesized from simple and inexpensive commercial starting materials, which is advantageous over semisynthetic naturally-derived compounds, which require significant crop production.

Yet another aspect of the invention is represented by compounds of for

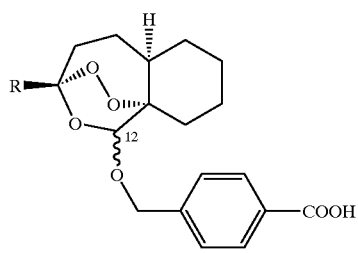

wherein R represents a substituted or unsubstituted aryl, alkyl or alkoxy group of 1–20, preferably 1–12, carbon atoms. Compounds wherein R represents a p-fluorophenyl, p-carboxyphenyl, p-HO$_3$S-phenyl, a methyl or an ethyl group are particularly preferred.

These compounds can be used according to a further embodiment of the invention for treatment of malaria and other parasitic infections by the administration of effective dosages to persons in need of such treatment. Suitable dosages are expected to be in the range of about 10 mg to 5 gm, preferably about 50 to 1000 mg administered over a period of 2–5 days, alone or in combination with other antimalarial drugs, such as, for example, benflumetol and other such drugs familiar to those of skill in the art. Examples of combination therapy are presented in Looareesuwan et al. (17) and combinations according to the invention will be evident to those of skill in the art.

These and other objects of the invention can be accomplished using the methods set forth in the following detailed examples.

DETAILED DESCRIPTION OF THE INVENTION EXPERIMENTAL

General. Unless otherwise noted: Reactions were run in flame-dried round-bottomed flasks under an atmosphere of ultra high purity (UHP) argon. Diethyl ether (ether) and tetrahydrofuran (THF) were distilled from sodium benzophenone ketyl prior to use. Methylene chloride (CH$_2$Cl$_2$) was distilled from calcium hydride prior to use. All other compounds were purchased from Aldrich Chemical Company and used without further purification. Analytical thin-layer chromatography (t.l.c.) was conducted with Silica Gel 60 F$_{254}$ plates (250 μm thickness, Merck). Column chromatography was performed using short path silica gel (particle size<230 mesh), flash silica gel (particle size 400–230 mesh), or Florisil® (200 mesh). Yields are not optimized. High performance liquid chromatography (HPLC) was carried out with a Rainin HPLX system equipped with two 25 mL/min preparative pump heads using Rainin Dynamax 10 mm×250 mm (semi-preparative) columns packed with 60 Å silica gel (8 μm pore size), either as bare silica or as C-18-bonded silica. Melting points were measured using a Mel-Temp metal-block apparatus and are uncorrected. Nuclear magnetic resonance (NMR) spectra were obtained either on a Varian XL-400 spectrometer, operating at 400 MHz for $^1$H and 100 MHz for $^{13}$C or on a Varian XL-500 spectrometer, operating at 500 MHz for $^1$H and 125 MHz for $^{13}$C. Chemical shifts are reported in parts per million (ppm, δ) downfield from tetramethylsilane. Splitting patterns are described as singlet (s), doublet (d), triplet (t), quartet (q), multiplet (m), and broad (b). Infrared (IR) spectra were obtained using a Perkin-Elmer 1600 FT-IR spectrometer. Resonances are reported in wavenumbers (cm$^{-1}$). Low resolution (LRMS) and high resolution (HRMS) mass spectra were obtained on a VG Instruments 70-S spectrometer run at 70 eV for electronic ionization (EI) and run with ammonia (NH$_3$) as a carrier for chemical ionization (CI). Combustion analyses were conducted by Atlantic Microlab (Norcross, Ga.). A preliminary report of several of the synthetic schemes described below has been published (12).

General Procedure 1

Trioxane Formation By Singlet Oxygenation

A sulfonation (3-necked) flask was fitted with a gas inlet line, an outlet line with stopcock, and a septum. To this flask was added solid methylene blue (ca. 5 mg) followed by a solution of the starting ketone (1.0 equivalents) in CH$_2$Cl$_2$ (0.01 M). The resulting solution was cooled to −78° C. while UHP oxygen passed through a drying column was bubbled (ca. 1 mL/s) through the solution. The reaction mixture was then irradiated with UV light (medium pressure Hg lamp) with continuous O$_2$ bubbling just until t.l.c. analysis showed >95% consumption of starting material. After irradiation, an argon source was introduced through the septum, the outlet stopcock was closed, and the gas inlet line was replaced with a stopper. To this reaction mixture, still at −78° C., was then added by cannula a −78° C. solution of t-BuMe$_2$SiOTf (1.1 equivalents) in CH$_2$Cl$_2$ (0.50 M). The resulting solution was stirred for 8 h at −78° C. At that time, the reaction was quenched by addition via syringe over 2 min of Et$_3$N (neat, 3.3 equivalents). The mixture was allowed to warm to room temperature (r.t.) slowly over at least 3 h and was then concentrated under reduced pressure to ca. 1 mL total volume.

General Procedure 2

Desilylation by Fluoride Ion

To a solution of starting silyl ether (1.0 equivalents) in THF (0.33 M) at 0° C. was added a 0° C. solution of Bu$_4$NF (monohydrate, 1.5 equivalents) in THF (0.67 M). The resulting solution was stirred at 0° C. until the starting material was consumed. The reaction was quenched with H$_2$O (3 mL) and then diluted with appropriate volumes of ether and H$_2$O. The organic phase was separated, and the aqueous phase was extracted with appropriate volumes ether. The organic portions were combined, washed with saturated aqueous NaCl, dried over anhydrous MgSO$_4$, filtered, and concentrated under reduced pressure.

Synthesis of C$_3$-Aryl Trioxanes

C$_3$-Aryl Trioxanes were synthesized according to the following general scheme:

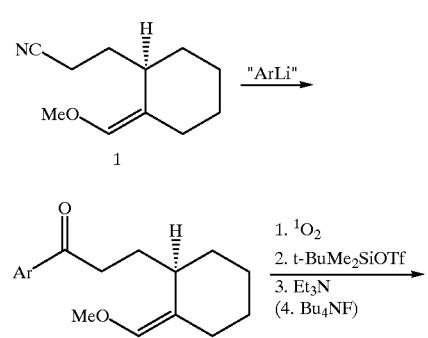

Scheme I:

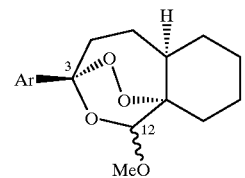

2: Ar = p-PhPh
3: Ar = p-FPh
4: Ar = p-F-o-MePh
5: Ar = p-MeO
6: Ar = p-(t-BuMe$_2$SiOCH$_2$)Ph
7: Ar = 2-furyl 8: Ar = p-PhPh
9: Ar = p-FPh
10: Ar = p-F-o-MePh
11: Ar = p-MeO
12: Ar = p-(HOCH$_2$)Ph
13: Ar = 2-furyl 4-Biphenyl Ketone 2

To a solution of 4-bromobiphenyl (770 mg, 3.30 mmol) in ether (4 mL) at 0° C. was added n-BuLi (2.5 mL, 1.25 M in hexanes, 3.1 mmol) via syringe. This solution was stirred at 0° C. for 5 min, then warmed to r.t. and stirred for 1 h. The resulting greenish grey turbid mixture was added dropwise via cannula (without cooling) to a −78° C. solution of nitrile 1 (370 mg, 2.06 mmol) in ether (14 mL). The reaction mixture turned bright orange and fumed extensively during the addition. The mixture was stirred at −78° C. for 5 min, then warmed to r.t. and stirred for 3 h. At that time, the reaction was quenched with H$_2$O (3 mL) and then diluted with ether (50 mL) and H$_2$O (50 mL). The organic phase was separated, and the aqueous phase was extracted with ether (50 mL×2). The organic portions were combined, washed with saturated aqueous NaCl, dried over anhydrous MgSO$_4$, filtered, and concentrated under reduced pressure. The crude product was purified by column chromatography (20 g short path, 1%→10% EtOAc/hexane) to give the desired product (282 mg, 2.53 mmol, 41%) as a light pink solid: m.p.= 93–94.5° C.; $^1$H NMR (400 MHz, CDCl$_3$) δ 8.02 (m, 2 H), 7.67 (m, 2H), 7.62 (m, 2 H), 7.46 (m, 2 H), 7.39 (m, 1 H), 5.81 (d, J=2.0 Hz 1 H), 3.43 (s, 3 H), 3.03–2.88 (m, 3 H), 2.03 (m, 2 H), 1.85–1.73 (m, 3 H), 1.64 (m, 1 H); 1.59–1.49 (m, 3 H), 1.22 (m, 1 H); $^{13}$C NMR (100 MHz, CDCl$_3$) δ 200.2, 145.1, 140.3, 139.8, 135.9, 128.8, 128.5, 128.0, 127.1, 126.9, 118.9, 59.0, 36.8, 32.6, 31.6, 28.2, 26.4, 25.8, 21.6; IR (CHCl$_3$) 3032, 3012, 2931, 2856, 1678, 1605, 1238, 1449, 1404, 1124 cm$^{-1}$; LRMS (EI, rel intensity) submitted; HRMS (EI) m/z submitted.

C$_3$-(4-Biphenyl) Trioxanes 8

4-Biphenyl ketone 2 (190 mg, 0.565 mmol) was treated according to General Procedure 1 (irradiation for 20 min). The crude reaction mixture was purified by column chromatography (ca. 15 g Florisil®, 1%→10% EtOAc/hexanes) to give C$_{12\alpha}$-OMe trioxane 8a (90 mg, 0.24 mmol, 43%) and C$_{12\beta}$-OMe trioxane 8b (45 mg, 0.324 mmol, 22%).

Further purification of 8a by HPLC (silica, 85% CH$_2$Cl$_2$/hexanes, 2.5 mL/min, 274 nm, R$_t$=15.8 min) afforded a white solid: $^1$H NMR (400 MHz, CDCl$_3$) δ 7.60 (m, 6 H), 7.43 (m, 2 H), 7.34 (m, 1 H), 5.20 (s, 1 H), 3.64 (s, 3 H), 2.87 (ddd, J=14.4, 13.2, 3.6 Hz, 1 H), 2.43 (m, 1 H), 2.33 (ddd, J=14.8, 4.8, 2.4 Hz, 1 H), 1.90 (m, 1 H), 1.84–1.68 (m, 4 H), 1.64 (m, 1 H), 1.33–1.18 (m, 4 H); $^{13}$C NMR (100 MHz, CDCl$_3$) δ 141.5, 140.5, 139.4, 128.7, 127.4, 127.1, 126.8, 125.8, 103.9, 96.1, 83.6, 56.0, 45.4, 37.5, 33.4, 32.5, 27.2, 25.3, 23.1; IR (CHCl$_3$) 3032, 3012, 2934, 2863, 1600, 1488, 1451, 1348, 1099, 1006 cm$^{-1}$.

Further purification of 8b by HPLC (silica, 3% EtOAc/hexanes, 3 mL/min, 274 nm, Rt=9.9 min) afforded a white solid: m.p.=146–147° C.; $^1$H NMR (400 MHz, CDCl$_3$) δ

7.60 (m, 6 H), 7.43 (m, 2 H), 7.35 (m, 1 H), 5.17 (d, J=1.2 Hz, 1 H), 3.67 (s, 3 H), 2.82 (ddd, J=14.8, 13.2, 3.6 Hz, 1 H), 2.36 (ddd, J=14.4, 4.4, 3.2 Hz, 1 H), 2.05–1.90 (m, 2 H), 1.82–1.62 (m, 7 H), 1.31 (dt, $J_d$=4.8 Hz, $J_t$=13.6 Hz, 1 H) overlapping 1.24 (m, 1 H); $^{13}$C NMR (100 MHz, CDCl$_3$) δ 141.6, 140.6, 139.7, 128.7, 127.4, 127.1, 126.9, 125.7, 105.1, 105.0, 83.8, 57.2, 47.5, 39.1, 35.7, 30.8, 26.9, 25.1, 23.9; IR (CHCl$_3$) 3035, 3011, 2933, 2862, 1600, 1487, 1447, 1219, 1138, 1103 cm$^{-1}$; Anal. calcd for C$_{23}$H$_{26}$O$_4$; C 75.37, H 7.16, found: C 74.90, H 7.19. Note that this combustion analysis rules out the deoxytrioxane product, anal. calcd for C$_{23}$H$_{26}$O$_3$; C 78.80, H 7.49.

ρ-Fluorophenyl Ketone 3

To a solution of nitrile 1 (900 mg, 5.02 mmol) in ether (45 mL) at 0° C. was added via syringe ρ-fluorophenylmagnesium bromide (5.0 mL, 2.0 M solution in ether 10 mmol). The resulting turbid mixture was stirred at 0° C. for 5 min then warmed to r.t. and stirred for 6 h. At that time, the reaction was quenched with H$_2$O (3 mL) and then diluted with ether (25 mL) and H$_2$O (25 mL). The organic phase was separated, and the aqueous phase was extracted with ether (80 mL×2). The organic portions were combined, washed with saturated aqueous NaCl, dried over anhydrous MgSO$_4$, filtered, and concentrated under reduced pressure. The crude product was purified by column chromatography (30 g short path, 1%→10% EtOAc/hexane) to give the desired product (700 mg, 2.53 mmol, 50%) as a pale yellow oil: $^1$H NMR (400 MHz, CDCl$_3$) δ 7.97 (m, 2 H), 7.11 (m, 2 H), 5.79 (d, J=2.0 Hz, 1 H), 3.41 (s, 3 H), 2.97–2.81 (m, 3 H), 2.00 (m, 2 H), 1.82 (m, 1 H), 1.74 (m, 2 H), 1.65 (m, 1 H), 1.53 (m, 3 H), 1.21 (m, 1 H); $^{13}$C NMR (100 MHz, CDCl$_3$) δ 199.0, 165.3 (d, J=253 Hz), 140.4, 133.7 (d, J=3.0 Hz), 130.4 (d, J=9.1 Hz), 118.8, 115.3 (d, J=22.0 Hz), 59.0, 36.6, 32.5, 31.6, 28.2, 26.4, 25.7, 21.6.

C$_3$-(ρ-Fluoro)phenyl Trioxanes 9

ρ-Fluorophenyl ketone 3 (270 mg, 0.977 mmol) was treated according to General Procedure 1 (irradiation for 15 min). The crude reaction mixture was purified by column chromatography (ca. 20 g Florisil®, 1%→10% EtOAc/hexanes) go give C$_{12α}$-OMe trioxane 9a (60 mg, 0.19 mmol, 20%) and C$_{12β}$-OMe trioxane 9b (100 mg, 0.324 mmol, 33%).

Further purification of 9a by HPLC (C-18, 10% water/methanol, 3 mL/min, 260 nm, Rt=9.3 min) afforded a white solid: m.p.=97–98° C.; $^1$H NMR (400 MHz, CDCl$_3$) δ 7.54 (m, 2 H), 7.03 (m, 2 H), 5.17 (s, 1 H), 3.61 (s, 3 H), 2.83 (ddd, J=14.4, 13.2, 3.6 Hz, 1 H), 2.41 (m, 1 H), 2.25 (ddd, J=14.4, 4.8, 2.4 Hz, 1 H), 1.89 (m, 1 H), 1.82–1.70 (m, 4 H), 1.62 (m, 1 H), 1.30–1.15 (m, 4 H); $^{13}$C NMR (100 MHz, CDCl$_3$) δ 162.8 (d, J=246 Hz), 136.4 (d, J=3.0 Hz) 127.4 (d, J=8.3 Hz), 115.0 (d, J=22.0 Hz), 103.6, 96.2, 83.6, 56.1, 45.3, 37.5, 33.3, 32.5, 27.1, 25.2, 23.1; IR (CHCl$_3$) 3032, 3005, 2934, 2863, 1604, 1512, 1452, 1235, 1101, 1013 cm$^{-1}$.

Further purification of 9b by HPLC (C-18, 2% water/methanol, 3 mL/min, 270 nm, Rt=6.3 min) afforded a white solid: m.p.=87–88° C.; $^1$H NMR (400 MHz, CDCl$_3$) δ 7.53 (m, 2 H), 7.03 (m, 2 H), 5.13 (d, J=1.2 Hz), 3.64 (s, 3 H), 2.78 (ddd, J=14.4, 13.2, 3.6 Hz, 1 H), 2.28 (ddd, J=14.4, 4.8, 3.2 Hz, 1 H), 2.01–1.87 (m, 2 H), 1.80–1.59 (m, 7H), 1.30 (dt, $J_d$=4.8 Hz, $J_t$=13.6 Hz, 1 H), 1.21 (m, 1 H); $^{13}$C NMR (100 MHz, CDCl$_3$) δ 162.8 (d, J=246 Hz), 136.7 (d, J=3.0 Hz), 127.2 (d, J=8.4 Hz), 115.0 (d, J=21.2 Hz), 105.1, 104.7, 83.7, 57.1, 47.4, 39.1, 35.6, 29.8, 25.0, 23.8; IR (CHCl$_3$) 3034, 3012, 2934, 2863, 1604, 1512, 1447, 1235, 1139, 1106 cm$^{-1}$.

ρ-Fluoro-o-methylphenyl Ketone 4

To a solution of ρ-fluoro-o-methylphenyl bromide (506 μL, 4.02 mmol) in ether (12 mL) at −78° C. was added via syringe t-BuLi (2.5 mL, 1.50 M solution in pentane, 3.8 mmol) over 1 min. This solution was stirred at −78° C. for 1 h, at which time is was milky white. To this mixture was added dropwise via cannula r.t. solution of nitrile 1 (450 mg, 2.51 mmol) in ether (10 mL). The reaction immediately turned bright yellow. The mixture was stirred at −78° C. for 15 min then warmed to r.t. over 1 h and stirred at that temperature for 2 h. The reaction was then quenched with H$_2$O (3 mL) and diluted with ether (10 mL) and H$_2$O (10 mL). The organic phase was separated, and the aqueous phase was extracted with ether (50 mL×2). The organic portions were combined, washed with saturated aqueous NaCl, dried over anhydrous MgSO$_4$, filtered, and concentrated under reduced pressure. The crude product was purified by column chromatography (15 g short path, 1%→20% EtOAc/hexane) to give the desired product (476 mg, 1.64 mmol, 65%) as a pale yellow oil: $^1$H NMR (400 MHz, CDCl$_3$) δ 7.66 (m, 1 H), 6.91 m, 2 H), 5.77 (d, J=2.0 Hz, 1 H), 3.38 (s, 3 H), 2.82 (m, 3 H), 2.50 (s, 3 H), 1.98 (m, 2 H), 1.80 (m, 1 H), 1.72 (m, 3 H), 1.64 (m, 1 H), 1.54 (m, 3 H) 1.20 (m, 1 H); $^{13}$C NMR (100 MHz, CDCl$_3$) δ 203.1, 163.6 (d, J=8.3 Hz), 140.4, 134.5 (d, J=3.1 Hz), 130.9 (d, J=9.1 Hz), 118.8, 118.4 (d, J=20.5 Hz), 112.2 (d, J=21.2 Hz), 59.0, 39.5, 32.5, 31.7, 28.2, 26.4, 25.8, 21.6, 21.5; IR (neat) 3067, 3001, 2928, 2853, 1686, 1604, 1583, 1448, 1238, 1124 cm$^{-1}$.

C$_3$-(ρ-Fluoro-o-methyl)phenyl Trioxanes 10

ρ-Fluoro-o-methylphenyl ketone 4 (230 mg, 0.792 mmol) was treated according to General Procedure 1 (irradiation for 20 min). The crude reaction mixture was purified by column chromatography (ca. 20 g Florisil®, 1%→20% EtOAc/hexanes) to give C$_{12α}$-OMe trioxane 10a (40 mg, 0.12 mmol, 16%) and C$_{12β}$-OME trioxane 10b (50 mg, 0.16 mmol, 20%).

Further purification of 10a by HPLC (silica, 4% EtOAc/hexanes, 3 mL/min, 254 nm, rt=13.7 min) afforded a white solid: m.p.=112–113° C.; $^1$H NMR (400 MHz, CDCl$_3$) δ 7.68 (m, 1 H), 6.84 (m, 2 H), 5.17 (s, 1 H), 3.53 (s, 3 H), 2.96 (ddd, J=14.4, 12.8, 4.0 Hz, 1 H), 2.46 (s, 3 H), 2.42 (m, 1 H), 2.10 (ddd, J=14.8, 4.4, 2.8 Hz, 1 H), 1.89 (m, 1 H), 1.78–1.60 (m, 5H), 1.30–1.16 (m, 4 H); $^{13}$C NMR (100 MHz, CDCl$_3$) δ 162.3 (d, J=246 Hz), 138.2 (d, J=7.6 Hz), 134.9 (d, J=3.1 Hz), 127.1 (d, J=8.3 Hz), 118.3 (d, J=21.2 Hz), 111.9 (d, J=20.4 Hz), 104.3, 95.9, 83.8, 55.8, 45.3, 36.9, 33.4, 32.5, 27.4, 25.3, 23.1, 21.3; IR (CHCl$_3$) 3031, 3004, 2934, 2863, 1612, 1592, 1495, 1451, 1264, 1240, 1100, 1016 cm$^{-1}$.

Further purification of 10b by HPLC (silica, 1% EtOAc/hexanes, 3 mL/min, 254 nm, R$_t$=10.4 min) afforded a white solid: m.p.=97–99° C.; $^1$H NMR (400 MHz, CDCl$_3$) δ 7.62 (m, 1 H), 6.85 (m, 2 H), 5.10 (d, J=0.8 Hz), 3.62 (s, 3 H), 2.85 (ddd, J=14.4, 13.2, 3.6 Hz, 1 H), 2.49 (s, 3 H), 2.22 (ddd, J=14.8, 4.0, 4.0 Hz, 1 H), 2.06–190 (m, 2 H), 1.81–1.59 (m, 7 H), 1.30 (dt, $J_d$=4.8 Hz, $J_t$=13.6 Hz, 1 H), 1.20 (m, 1 H); $^{13}$C NMR (100 MHz, CDCl$_3$) δ 162.3 (d, J=246 Hz), 138.4 (d, J=8.4 Hz), 135.1 (d, J=3.1 Hz), 127.3 (d, J=8.4 Hz), 118.4 (d, J=20.5 Hz), 111.9 (d, J=19.7 Hz), 105.7, 104.6, 84.0, 57.1, 47.4, 38.3, 35.6, 30.7, 27.0, 25.0, 23.8, 21.5; IR (CHCl$_3$) 3034, 3009, 2934, 2862, 1613, 1591, 1495, 1447, 1270, 1244, 1105, 1021 cm$^{-1}$.

ρ-Methoxyphenyl Ketone 5

To a solution of ρ-methoxyphenyl bromide (336 μL, 2.68 mmol) in ether (6 mL) at −78° C. was added via syringe t-BuLi (1.8 mL, 1.40 M solution in pentane, 2.5 mmol). The resulting mixture was stirred for 30 min at −78° C., at which time a −78° C. solution of nitrile 1 (300 mg, 1.67 mmol) in ether (8 mL) was added via cannula. This mixture was stirred at −78° C. for 15 min, warmed to r.t. over 1 h, and stirred at this temperature for 4 h. The reaction was then quenched with $H_2O$ (3 mL) and diluted with ether (20 mL) and $H_2O$ (20 mL). The organic phase was separated, and the aqueous phase was extracted with ether (50 mL×2). The organic portions were combined, washed with saturated aqueous NaCl, dried over anhydrous $MgSO_4$, filtered, and concentrated under reduced pressure. The crude product was purified by column chromatography (15 g flash gel, 1%→20% EtOAc/hexane) to give the desired product (323 mg, 1.12 mmol, 67%) as a colorless oil: $^1H$ NMR (400 MHz, $CDCl_3$) δ 7.93 (m, 2 H), 6.92 (m, 2 H), 5.80 (d, J−1.6 Hz, 1 H), 3.86 (s, 3 H), 3.43 (s, 3 H), 2.94–2.80 (m, 3 H), 2.05–1.94 (m, 2 H), 1.81 (M, 1 H), 1.74 (m, 2 H), 1.64 (m, 1 H), 1.59–1.48 (m, 3 H), 1.28–1.16 (m, 1 H); $^{13}C$ NMR (100 MNz, $CDCl_3$) δ 199.3, 162.9 140.2, 130.2, 130.0, 118.9, 13.4, 59.0, 55.2, 36.4, 32.6, 31.6, 28.2, 26.3, 25.9, 21.5; IR (neat) 3056, 3003, 2926, 2852, 1675, 1601, 1510, 1257, 1170, 1123 $cm^{-1}$.

$C_3$-(ρ-Methoxy)phenyl Trioxane 11

ρ-Methoxyphenyl ketone 5 (300 mg, 1.04 mmol) was treated according to General Procedure 1 (irradiation for 50 min). The crude reaction mixture was purified by column chromatography (ca. 30 g Florisil®, 1%→10% EtOAc/hexanes) to give trioxane 11 (140 mg, 0.437 mmol, 42%). The relative stereochemistry of this analog is ambiguous.

Further purification of 11 by HPLC (silica, 5% EtOAc/hexanes, 3 mL/min, 254 nm, Rt=19.0 min) afforded a white solid: m.p.=84.5–85° C.; $^1H$ NMR (400 MHz, $CDCl_3$) δ 7.19 (m, 2 H), 6.79 (m, 2 H), 4.80 (s, 1 H), 3.77 (s, 3 H), 3.18 (s, 3 H), 2.11 (m, 1 H), 2.02–1.91 (m, 2 H), 1.69 (m, 4 H), 1.60 (m, 1 H), 1.50–1.38 (m, 2 H), 1.28 (m, 1 H), 1.19–1.05 (m, 2 H); $^{13}C$ NMR (100 MHz, $CDCl_3$) δ 155.8, 146.1, 123.1, 120.8, 113.4, 99.5, 85.5, 55.4, 54.6, 39.9, 33.3, 30.2, 29.7, 25.7, 25.3, 22.8; IR ($CHCl_3$) 3029, 3012, 2938, 1506, 1450, 1342, 1180, 1202, 1129, 997 $cm^{-1}$; Anal. calcd for $C_{18}H_{24}O_5$; C 67.47, H 7.57, found: C 67.54, H 7.57. Note that this combustion analysis rules out the deoxytrioxane product, anal. calcd for $C_{18}H_{24}O_4$; C 71.02, H 7.96.

t-Butyldimethylsilyl-protected ρ-hydroxymethylphenyl Bromide.

To a solution of ρ-bromobenzyl alcohol (ρ-hydroxymethylphenyl bromide, 1.00 g, 5.35 mmol) in $CH_2Cl_2$(50 mL) at 0° C. were added, both via syringe, 2,6-lutidine (930 μL, 8.02 mmol) and, 1 min later, t-butyldimethylsilyl triflate (1.6 mL, 7.0 mmol). The resulting solution was stirred for 1 h at 0° C. The reaction was then quenched with $H_2O$ (3 mL) and diluted with ether (100 mL) and $H_2O$ (100 mL). The organic phase was separated, and the aqueous phase was extracted with ether (100 mL×2). The organic portions were combined, washed with saturated aqueous NaCl, dried over anhydrous $MgSO_4$, filtered, and concentrated under reduced pressure. The crude product was purified by column chromatography (40 g short path, 1% EtOAc/hexane) to give the desired product (1.56 g, 5.16 mmol, 96%) as a colorless oil: $^1H$ NMR (400 MHz, $CDCl_3$) δ 7.45 (m, 2 H), 7.20 (m, 2 H), 4.69 (s, 2 H), 0.95 (d, J=0.8 Hz, 9 H), 0.11 (d, J=0.8 Hz, 6 H); $^{13}C$ NMR (100 MHz, $CDCl_3$) δ 140.4, 131.2, 127.6, 120.5, 64.3, 25.9, 18.4, −5.2; IR (neat) 3028, 2929, 2885, 2857, 1593, 1487, 1471, 1257, 1087, 1012, 839, 778 $cm^{-1}$.

t-Butyldimethylsilyl-protected ρ-hydroxymethylphenyl Ketone 6

To a solution of the above aryl bromide (2.53 g, 8.37 mmol) in ether (25 mL) at −78° C. was added via syringe t-BuLi (5.2 mL, 1.50 M solution in pentane, 7.8 mmol). The resulting mixture was stirred at −78° C. for 45 min, at which time it was yellow and turbid. A r.t. solution of nitrile 1 (1.00 g, 5.58 mmol) in ether (25 mL) was then added via cannula. This reaction mixture was stirred at −78° C. for 15 min, warmed to r.t. over 1 h, and stirred at r.t. for 2 h. The reaction was then quenched with $H_2O$ (3 mL) and diluted with ether (50 mL) and $H_2O$ (50 mL). The organic phase was separated, and the aqueous phase was extracted with ether (100 mL×2). The organic portions were combined, washed with saturated aqueous NaCl, dried over anhydrous $MgSO_4$, filtered, and concentrated under reduced pressure. The crude product was purified by column chromatography (40 g flash gel, 1→10% EtOAc/hexane) to give the desired product (1.21 g, 3.00 mmol, 54%) as a colorless oil: $^1H$ NMR (400 MHz, $CDCl_3$) δ 7.92 (m, 2 H), 7.39 (m, 2 H), 5.79 (d, J=1.6 Hz, 1H), 4.78 (s, 2 H), 3.41 (s, 3 H), 2.99–2.83 (m, 3 H), 2.00 (m, 2 H), 1.80 (m, 1 H), 1.74 (m, 2 H), 1.65 (m, 1 H), 1.52 (m, 3 H), 1.26–1.15 (m, 1 H), 0.95 (s, 9 H), 0.11 (s, 6 H); $^{13}C$ NMR (100 MHz, $CDCl_3$) δ 200.4, 146.3, 140.3, 136.0, 128.0, 125.6, 118.9, 64.4, 59.0, 36.8, 32.6, 31.6, 28.2, 26.4, 25.8, 21.6, 18.3, −5.3; IR (neat) 3055, 3001, 2928, 2856, 1684, 1609, 1462, 1256, 1124, 1094, 839, 778 $cm^{-1}$.

$C_3$-(ρ-hydroxymethyl)phenyl Trioxanes 12 t-Butyldimethylsilyl-protected ρ-hydroxy-methylphenyl ketone 6 (405) mg, 1.00 mmol) was treated according to General Procedure 1 (irradiation for 25 min). The crude reaction mixture was purified by column chromatography (ca. 30 g Florisil®, 1%→20% EtOAc/hexanes) to give a silylated $C_{12\alpha}$-OME trioxane (110 mg, 0.252 mmol, 25%) and a silylated $C_{12\beta}$-OMe trioxane (90 mg, 0.21 mmol, 21%). These trioxanes (100 mg, 0.230 mmol of $C_{12\alpha}$-OMe analog; 75 mg, 0.17 mmol of $C_{12\beta}$-OME analog) were individually desilylated according to General Procedure 2 (2 h for $C_{12\alpha}$-OMe analog; 3 h for $C_{12\beta}$-OMe analog). The resulting crude products were purified separately by column chromatography (ca. 10 g Florisil® each, 5%→50% EtOAc/hexanes) to give $C_{12\alpha}$-OMe trioxane 12a (60 mg, 0.19 mmol, 0.19 mmol, 83%) and $C_{12\beta}$-OMe trioxane 12b (40 mg, 0.12 mmol, 71%).

Further purification of 12a by HPLC (silica, 10% i-PrOH/hexanes, 3 mL/min, 254 nm, $R_t$=14.4 min) afforded a white solid: $^1H$ NMR (400 MHz, $CDCl_3$) δ 7.54 (m, 2 H), 7.34 (m, 2 H), 5.18 (s, 1 H), 4.68 (s, 2 H), 3.61 (s, 3 H), 2.83 (ddd, J=14.4, 13.6, 4.0 Hz, 1 H), 2.41 (m, 1 H), 2.26 (ddd, J=14.8, 4.8, 2.4 Hz, 1 H), 1.89 (m, 1 H), 1.82–1.69 (m, 5 H), 1.67–1.56 (m, 1 H), 1.33–1.15 (m, 4 H); $^{13}C$ NMR (100 MHz, $CDCl_3$) δ 141.4, 139.7, 126.5, 125.5, 103.8, 96.0, 83.6, 64.8, 55.9, 45.3, 37.5, 33.3, 32.5, 27.1, 25.2, 23.1; IR ($CHCl_3$) 3608, 3506, 3031, 3012, 2934, 2864, 1451, 1347, 1272, 1100, 1012, 972 $cm^{-1}$.

Further purification of 12b by HPLC (silica, 5% i-PrOH/hexanes, 3 mL/min, 254 nm, $R_t$=18.6 min) afforded a colorless oil: $^1H$ NMR (400 MHz, $CDCl_3$) δ 7.55 (m, 2 H), 7.35 (m, 2 H), 5.14 (d, J=1.2 Hz, 1 H), 4.69 (d, J=3.2 Hz, 2 H), 3.65 (s, 3 H), 2.78 (ddd, J=14.8, 13.2, 3.6 Hz, 1H), 2.29 (ddd, J=14.4, 4.4, 3.2 Hz, 1 H), 2.02–1.89 (m, 2 H), 1.81–1.59 (m, 8 H), 1.30 (dt, $J_d$=4.8 Hz, $J_t$=13.6 Hz, 1 H), 1.20 (m, 1 H); $^{13}C$ NMR (125 MHz, $CDCl_3$) δ 141.4, 140.1, 126.7, 125.5, 105.1, 105.0, 83.8, 64.9, 57.1, 47.4, 39.1, 35.6, 30.8, 26.8, 25.0, 23.8; IR ($CHCl_3$) 3608, 3473, 3031, 3012, 2933, 2863, 1446, 1277, 1139, 1104, 1036, 960 $cm^{-1}$.

Further derivatives of trioxane 12b can be prepared according to the following scheme, as will be evident to persons of skill in the art.

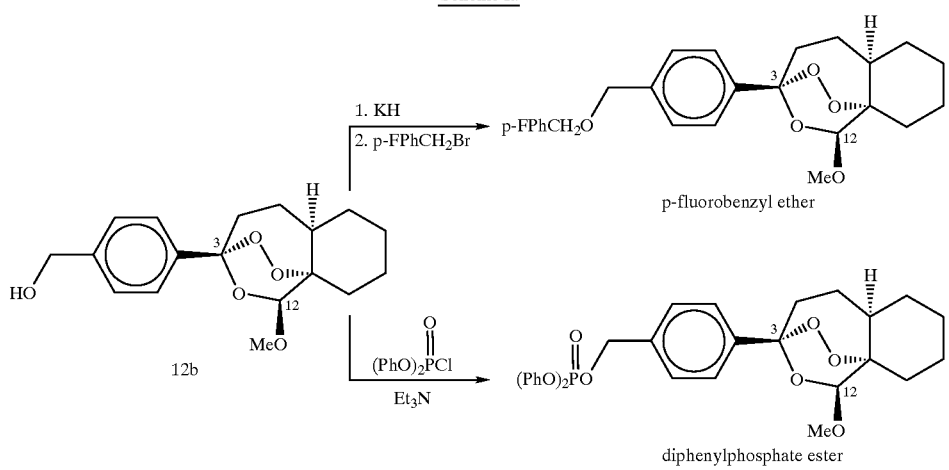

2-Furyl Ketone 7

To a solution of furan (525 μL, 7.25 mmol) in THF (8 mL) at 0° C. was added via syringe n-BuLi (5.6 mL, 1.25 M solution in hexanes, 7.0 mmol). The mixture was stirred at 0° C. for 12 h then warmed to r.t. and stirred for 1 h. This solution was then cooled back to 0° C. and a solution of nitrile 1 (500 mg, 2.79 mmol) in THF (4 mL) at 0° C. was added via cannula. The reaction immediately turned bright orange. After 5 min at 0° C., the mixture was warmed to r.t. and stirred for 6 h, at which time it was dark red. The reaction was then quenched with $H_2O$ (3 mL) and then diluted with ether (20 mL) and $H_2O$ (20 mL). The organic phase was separated, and the aqueous phase was extracted with ether (50 mL×2). The organic portions were combined, washed with saturated aqueous NaCl, dried over anhydrous $MgSO_4$, filtered, and concentrated under reduced pressure. The crude product was purified by column chromatography (20 g flash gel, 1%→20% EtOAc/hexane) to give the desired product (296 mg, 1.19 mmol, 43%) as a yellow oil: $^1$H NMR (400 MHz, $CDCl_3$) δ 7.56 (dd, J=1.6, 0.8 Hz), 7.15 (dd, J=3.6, 0.8 Hz), 6.51 (dd, J=3.6, 1.6 Hz), 5.79 (d, J=2.0 Hz), 3.44 (s, 3 H), 2.86 (m, 1 H), 2.83–2.70 (m, 2 H), 1.99 (m, 2 H), 1.81 (m, 1 H), 1.73 (m, 2 H), 1.73 (m, 2H), 1.63 (m, 1 H), 1.52 (m, 3 H), 1.20 (m, 1 H); $^{13}$C NMR (100 MHz, $CDCl_3$) δ 190.0, 152.8, 145.9, 140.3, 118.9, 116.5, 111.9, 59.1, 36.8, 32.6, 31.5, 28.2, 26.4, 25.7, 21.6; IR (neat) 3133, 3001, 2926, 2853, 1677, 1569, 1469, 1240, 1202, 1124 $cm^{-1}$;

$C_3$-(2-Furyl) Trioxane 13

2-Furyl ketone 7 (250 mg, 1.01 mmol) was treated according to General Procedure 1 (irradiation for 35 min). The crude reaction mixture was purified by column chromatography (ca. 30 g Florisil®, 1%→20% EtOAc/hexanes) to give $C_{12\alpha}$-OMe trioxane 13 (45 mg, 0.16 mmol, 16%).

Further purification of 13 by HPLC (silica, 5% EtOAc/hexanes, 4 mL/min, 254 nm, $R_t$=14.2 min) afforded a white solid: m.p.=110.5–112° C.; $^1$H NMR (400 MHz, $CDCl_3$) δ 7.41 (dd, J=1.6, 0.8 Hz), 6.54 (dd, J=3.2, 0.8 Hz), 6.37 (dd, J=3.2, 1.6 Hz), 5.12 (s, 1 H), 3.64 (s, 3 H), 2.75 (ddd, J=14.8, 13.2, 3.6 Hz, 1 H), 2.53 (ddd, J=14.8, 4.8, 2.8 Hz, 1 H), 2.40 (m, 1 H), 1.89 (m, 1 H), 1.81–1.69 (m, 4 H), 1.66–1.54 (M, 1 H), 1.30–1.15 (m, 4 H); $^{13}$C NMR (100 MHz, $CDCl_3$) δ 151.2, 143.2, 110.5, 109.3, 100.8, 96.4, 83.6, 55.8, 45.4, 34.1, 33.3, 32.5, 26.5, 25.3, 23.2; IR ($CHCl_3$) 3032, 3012, 2934, 2863, 1452, 1348, 1103, 1041, 941 $cm^{-1}$.

Syntheses of other compounds of the invention can be carried out by addition of particular substituents to common precursor molecules, as will be evident to persons of ordinary skill in the art.

Synthesis of $C_3$-Alkyl Trioxanes $C_3$-alkyl trioxanes were synthesized according to the following general scheme:

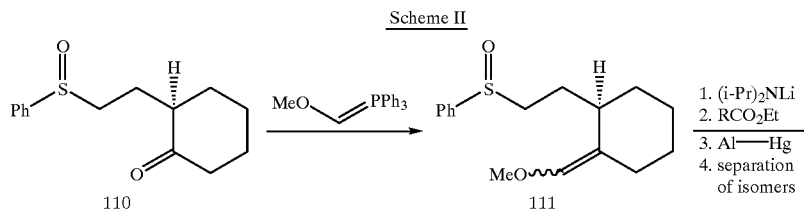

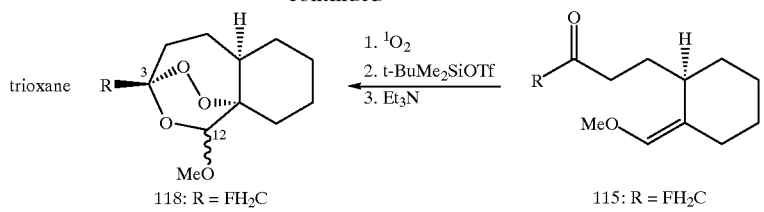

118: R = FH₂C   115: R = FH₂C

Sulfoxide Enol Ether 111

To a suspension of (methoxymethyl)triphenylphosphonium chloride (1.42 g, 4.14 mmol) in THF (15 mL) at −78° C. was added dropwise via syringe PhLi (2.34 mL, 1.77 M, 4.14 mmol). The resulting mixture was warmed to r.t. and stirred for 3 h. The resulting dark red solution was cooled to −78° C. and a solution of cyclohexanone sulfoxide 110 in THF (10 mL) was added dropwise by cannula. The resulting mixture was then allowed to warm to r.t. over 5 h, stirred for additional 5 h. At that time, the reaction was quenched with $H_2O$ (25 mL), extracted with EtOAc, dried over anhydrous $MgSO_4$, and concentrated. Purification by column chromatography (flash gel, 50% EtOAc/hexane) afforded the desired sulfone enol ether 111 (644 mg, 2.32 mmol, 89%) as a roughly equal mixture of four diastereomers: $^1H$ NMR (400 NMR (400 MHz, $CDCl_3$) δ 7.60 (m, 8 H), 7.51 (m, 12 H), 5.81 (s, 1 H), 5.80 (s, 1 H), 5.71 (s, 1 H), 5.69 (s, 1 H), 3.53 (s, 3 H), 3.52 (s, 3 H), 3.49 (s, 3 H), 3.47 (s, 3 H), 2.96 (m, 1 H), 2.75 (m, 8 H), 2.25 (m, 2 H), 2.10–1.20 (m, 41 H).

Fluoromethyl ketone 115

To a solution of diisopropylamine (850 μL, 6.08 mmol) in dry THF (20 mL) at −78° C. was added dropwise via syringe n-BuLi (3.5 ML, 1.60 M in hexanes, 5.6 mmol) and the resulting mixture was stirred for 30 min. To this solution of lithium diisopropylamide was added dropwise by cannula a solution of sulfoxide enol ether 111 (1.41 g, 5.07 mmol) in THF (7 mL) at −78° C. The mixture was allowed to warm to −35° C. over 2 h, stirred for an additional hour, and then cooled back to −78° C. A solution of ethyl fluoroacetate (750 mg, 7.10 mmol) in THF (2 mL) was added via cannula. The resulting reaction mixture was stirred at −78° C. for 1 h and then allowed to warm to −35° C. over 2 h. After being stirred at that temperature for an additional 2 h, the reaction was quenched with saturated aqueous ammonium chloride (30 mL). The mixture was extracted with EtOAc, dried over anhydrous $MgSO_4$, and concentrated to give a crude acylated sulfoxide, which was directly used for the next step without purification.

Aluminum foil (1.37 g) was cut into small strips, submerged in an aqueous 2% mercury(II) chloride solution for 15 s, rinsed well first with absolute ethanol and then with diethyl ether. The resulting aluminum/mercury amalgam was snipped with scissors into a 0° C. solution of acylated sulfoxide (from above) in aqueous THF (90 mL, THF:$H_2O$=9:1). This reaction was stirred at 0° C. for 1.5 h. Anhydrous $MgSO_4$ was added to the resulting grey slurry and this mixture was filtered with copius ether rinses. The combined organic washes were concentrated to give the crude product, which was purified by column chromatography (flash gel, 90% EtOAc/hexane) to afford pure ketone 115 (286 mg, 1.33 mmol, 26%) and the corresponding E-enol ether contaminated with ca. 10% of ketone 115 (370 mg mixture, 1.72 mmol, 34%). Fluoromethyl ketone 115: $^1H$ NMR (400 MHz, $CDCl_3$) δ 5.80 (d, J=2.0 Hz, 1 H), 4.79 (d, J=47.6 Hz, 2 H), 3.49 (s, 1 H) 2.79 (m, 1 H), 2.55–2.36 (m, 2 H), 2.00–1.45 (m, 9 H), 1.20 (m, 1 H); $^{13}C$ NMR (100 MHz, $CDCl_3$) δ 207.0 (d, J=18.2 Hz), 140.5, 118.6, 84.8 (d, J=184 Hz), 59.0, 36.1, 32.2, 31.6, 28.1, 26.2, 24.1, 21.5; IR (neat) 2928, 1738, 1677, 1233, 1124 $cm^{-1}$.

$C_3$-Fluoromethyl Trioxanes 118

Fluoromethyl ketone 115 (281 mg, 1.31 mmol) was treated according to General Procedure 1 (only 20 mL $CH_2Cl_2$, irradiation for 2 h). The crude reaction mixture was purified by column chromatography (flash gel, 90% EtOAc/hexanes) to give $C_{12\alpha}$-OMe trioxane 118a (132 mg, 0.536 mmol, 41%) and $C_{12\beta}$-OMe trioxane 118b (17 mg, 0.069 mmol, 5%).

Trioxane 118a: m.p.=80–81° C.; $^1H$ NMR (400 MHz, $CDCl_3$) δ 4.97 (s, 1 H), 4.25 (d ABq, $J_{d(H-F)}$=47.2 Hz, $\Delta V_{AB}$=18.7 Hz, $J_{AB}$=10.0 Hz, 2 H), 3.52 (s, 3 H), 2.35–2.22 (m, 1 H), 2.12 (m, 1 H), 1.85 (m, 2 H), 1.75–1.60 (m, 7 H), 1.34–1.15 (m, 2 H); $^{13}C$ NMR (100 MHz, $CDCl_3$) δ 104.8, 103.7 (d, J=19.8 Hz), 84.2, 83.8 (d, J=181 Hz), 57.2, 47.3, 35.4, 33.0, 30.8, 25.8, 24.9, 23.7.

Trioxane 118b: $^1H$ NMR (400 MHz, $CDCl_3$) δ 5.01 (d, J=0.8 Hz, 1 H), 4.24 (d ABq, $J_{d(H-F)}$=46.8 Hz, $\Delta V_{AB}$=15.0 Hz, $J_{AB}$=10.0 Hz, 2 H), 3.51 (s, 3 H), 2.34 (m, 2 H), 2.06 (m, 1 H), 1.85 (m, 1 H), 1.75–1.66 (m, 4 H), 1.54–1.42 (m, 1 H), 1.30–1.15 (m, 4 H); 13C NMR (100 MHz $CDCl_3$) δ 102.5 (d, J=20.5 Hz), 84.4 (d, J=181 Hz), 95.5, 84.2, 55.6, 45.3, 33.2, 32.5, 31.5, 26.2, 25.2, 23.0.

$C_3$-Fluoroalkyl and $C_3$-Fluorophenyl 1,2,4-trioxanes can be prepared according to the following scheme:

Scheme III

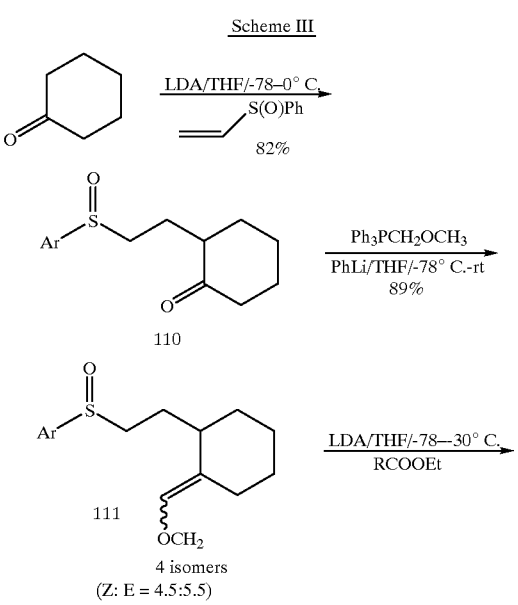

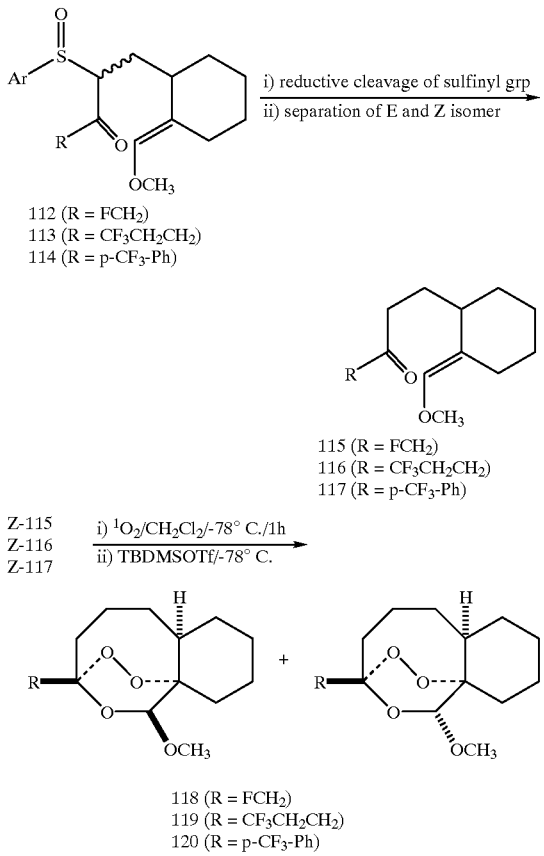

112 (R = FCH₂)
113 (R = CF₃CH₂CH₂)
114 (R = p-CF₃-Ph)

115 (R = FCH₂)
116 (R = CF₃CH₂CH₂)
117 (R = p-CF₃-Ph)

Z-115
Z-116
Z-117 i) ¹O₂/CH₂Cl₂/-78° C./1h
ii) TBDMSOTf/-78° C.

118 (R = FCH₂)
119 (R = CF₃CH₂CH₂)
120 (R = p-CF₃-Ph)

Ketophenyl Sulfoxide 110

To a solution of diisopropylamine (3.08 mL, 22 mmol) in dry THF (30 mL) was added dropwise 1.6M n-butyllithium (13.2 mL, 21 mmol) at −78° C. and the resulting solution was stirred for 30 min. To this LDA solution was added dropwise by cannula a solution of cyclohexanone (2.06 g, 21 mmol) in THF (30 mL) at −78° C. and the cooling bath was removed. After being stirred for 1 h, this solution was recooled to −78° C. A solution of phenyl vinyl sulfoxide (Aldrich, 3.34 g, 22 mmol) in THF (20 mL) was added, and the mixture was 4 allowed to reach rt over 5 h. Aqueous NaOH solution (1.0 N, 100 ml) was added, and the resulting mixture was stirred at rt for 1 h. The mixture was extracted with ethyl acetate, dried over anhydrous magnesium sulfate, and concentrated to give the crude product. Purification by silica gel chromatography (1:3=hexane:ethyl acetate) afforded 4.30 g (82%) of the desired keto phenyl sulfoxide 110 as inseparable mixture of the two diastereomers. ¹H NMR (400 MHz, CDCl₃); δ 1.30–2,55 (m, 11H), 2.72 (ddd,1H, J=5.2, 10.4, 12.8 Hz), 2.89–3.02 (m, 2H), 7.49–7.62 (m, 5H).

Ref. Montgomery, M. and Overman, L. E. J. Org. Chem. 1993, 58, 6476.

Methoxyvinyl Sulfoxide 111

To a suspension of methoxymethyl triphenylphosphonium chloride (1.42 g, 4.14 mmol) in dry THF (15 mL) at −78° C. was added dropwise a 1.77M phenyllithium solution (2.34 mL, 4.14 mmol), and the cooling bath was removed. Stirring was continued for 3 h to give a deep red solution. This solution was cooled to −78° C., and a solution of keto phenyl sulfoxide 110 in THF (10 mL) was added dropwise by cannula. The resulting mixture was then allowed to warm to rt over 5 h, stirred for an additional 5 h, and quenched with water (25 mL). The mixture was extracted with ethyl acetate, dried over anhydrous magnesium sulfate, and concentrated to give the crude product. Purification by silica gel chromatography (1:1=hexane: ethyl acetate) afforded 0.644 g (89%) of the desired product 111 as a mixture of the four diastereomers. ¹H NMR (400MHz, CDCl₃); δ 1.20–2.98 (m, 13H), 3.47, 3.49, 3.52, 3.53 (s, 3H), 5.69, 5,71, 5.80. and 5.81 (br s, 1H), 7.22–7.66 (m, 5H).

Fluoromethyl Ketone 115

To a solution of diisopropylamine (0.85 mL, 6.08 mmol) in dry THF (20 mL) was added dropwise 1.6M n-butyllithium (3.50 mL, 5.58 mmol) at −78° C. and the resulting solution was stirred for 30 min. To this LDA solution was added dropwise by cannula a solution of sulfoxide 111(1.41 g, 5.07 mmol) in THF (7 mL) at −78° C. The mixture was allowed to warm to −35° C. over 2 h, stirred at the same temperature for additional 1 h, and then cooled to −78° C. A solution of ethyl fluoroacetate (0.75 g, 7.10 mmol) in THF (2ml) was added, and the reaction mixture was stirred at −78° C. for 1 h and then allowed to warm to −35° C. over 2 h. After being stirred at −35° C. for an additional 2 h, the reaction was quenched with a saturated ammonium chloride solution (30 mL). The mixture was extracted with ethyl acetate, dried over anhydrous magnesium sulfate, and concentrated to give the crude product 112, which was directly used for the next step without purification. The crude 112 obtained above was dissolved in 90 mL of aqueous THF solution (THF: H₂O=9:1) and cooled to 0° C. A 1.37 g sample of aluminum foil was cut into small strips, submerged in aqueous 2% mercury(II) chloride solution for 15 sec, rinsed well with absolute ethanol and then diethyl ether. The resulting aluminum amalgam was snipped with scissors into the cold reaction mixture and stirring was continued at 0° C. for 1.5 h. Anhydrous magnesium sulfate was added to the resulting gray slurry and the mixture was filtered off. The slurry was rinsed well with diethyl ether. The combined organic layer was concentrated to give the crude product, which was purified by silica gel chromatography (hexane: ethyl acetate=10:1) to afford 0.286 g (26%) of the pure Z-115, along with 0.370 g (34%) of the corresponding E-isomer contaminated with ca. 10% of Z-115. Z115: ¹H NMR (400 MHz, CDCl₃); δ 1.50–1.98 (m, 12H), 2.36–2.56 (m, 2H), 2.80 (m, 1H), 3.49 (s, 3H), 4.79 (d, 2H, JCH₂—F=47.6 Hz), 5.80 (d, 1H, J=2.0 Hz). ¹³C NMR (100 MHz, CDCl₃); δ 21.5, 24.1, 26.2, 28.1, 31.6, 32.2, 36.1, 59.0, 84.8 (d, JCH₂—F=184 Hz), 118.6, 140.5, 207.0 (d, JCO-F=18 Hz) IR(film); 2928, 1738, 1677, 1233, 1124 cm⁻¹. E-113: ¹H NMR (400 MHz, CDCl₃); δ 1.20–2.60 (m, 15H), 3.52 (s, 3H), 4.77 (d, 2H, JCH₂—F=47.6 Hz), 5.70 (s, IH). ¹³C NMR (100 MHz, CDC₃); δ 22.4, 22.8, 24.5, 27.1, 33.3. 36.5, 38.4, 59.3, 84.9 (d, JCH2-F=184 Hz), 119.4, 139.6, 207.2 (d, JCO—F=19 Hz).

Trifluoropropyl Ketone 116

Following the same procedure described for the preparation of 112, sulfoxide enol ether 111 (1.20 g, 4.32 mmol), diisopropylamine (0.72 mL, 5.16 mmol), n-butyl lithium (2.96 mL, 4.73 mmol of a 1.6M solution), and ethyl 4,4,4,-trifluorobutyrate (1.02 g, 6.02 mmol). were employed to produce, after purification by silica gel column chromatography (hexane:ethyl acetate=3:1), 0.495 g (29%) of an acylated product 113 as a mixture of diasteromers, along with 0.597 g of unreacted starting compound 111. The acylated product (0.470 g, 1.175 mmol) was treated with aluminum amalgam (prepared from aluminum foil) (0.317 g) and an aqueous 2% mercury (II) chloride solution) at 0° C. in aqueous THF (30 mL, THF: H₂O=9:1). Anhydrous magnesium sulfate was added to the resulting gray slurry and the mixture was filtered off. The mixture was then allowed to warm to rt over 2 h. The slurry was rinsed well with diethyl ether. The combined organic layer was concentrated to give the crude product, which was purified by silica gel chromatography (hexane: ethyl acetate=10:1) to afford 0.12 g (37%) of the pure Z-116, along with 0.15 g (46%) of the corresponding E-isomer. Z-116:1 H NMR (400 MHz, CDCl$_3$); δ 1.20–1.98 (m, 10H), 2.38 (m, 4H), 2.66 (m, 2H), 2.75 (m,1H), 3.48 (s, 3H), 4.79 (d, 2H, JCH$_2$—F=47.6 Hz), 5.80 (d, 1H, J=2.0 Hz). $^{13}$C NMR; δ 21.6, 25.2, 26.4, 27.9 (q, J=29,8 Hz), 28.2, 31.7, 32.3, 35.0 (q, J=2.2 Hz), 40.5, 59.1, 118.8, 127.0 (q, J=276.2 Hz), 140.4, 207.6. E-116:$^1$H NMR (400 MHz, CDC13); δ 1.20–2.42(m, 15H), 2.67 (m,2H), 3.54 (s, 3H), 5.70 (s, IH). $^{13}$C NMR (100 MHz, CDCl$_3$); δ 22.4, 22.8, 25.4, 27.2, 27.9(q, J=29.6 Hz), 33.4, 35.0(q, J=2.3 Hz), 38.4, 41.1, 59.4, 1 19.5, 126.9 (q, J=274.6 Hz), 139.6, 207.2.

p-Trifluoromethylphenyl Ketone 117

Following the same procedure described for the preparation of 112, sulfoxide enol ether 111 (0.79 g, 2.84 mmol), diisopropylamine (0.48 ml, 3.41 mmol), n-butyllithium (1.95 mL, 3.12 mmol of a 1.6M solution), and methyl p-trifluoromethyl benzoate (0,75 g, 3.69 mmol) were employed to produce, after purification by silica gel column chromatography (hexane:ethyl acetate=3:1), 1.03 g (91%) of an acylated product 114 as a mixture of diasteromers. 114 (0.88 g, 1.955 mmol) was then dissolved in a 40 mL of THF-saturated NH$_4$Cl (1:1) solution and treated with activated zinc at rt. After being stirred for 2 h at rt, the reaction mixture was diluted with 40 mL of hexane-ethyl acetate (1:1) and washed with saturated sodium bicarbonated solution. The organic layer was dried over anhydrous magnesium sulfate and concentrated to give the crude product, which was purified by silica gel chromatography (hexane: ethyl acetate=15:1) to afford 0.121 g (19%) of the pure Z-117, along with 0.149 g (23%) of E-isomer contaminated ca. 15% of the corresponding Z isomer. Z-117: $^1$H NMR (400 MHz, CDCl$_3$); δ 1.21 (m, 1H), 1.53–2.07 (m, 9H), 2.85–3.02 (m, 3H), 3.38 (s, 3H), 5.77 (d, 1H, J=1.6 Hz), 7.70 (m, 2H), 8.03 (m, 2H). $^{13}$C NMR (100 MHz, CDCl$_3$); δ 21.7, 25.6, 26.4, 28.2, 31.7, 32.5, 37.1, 59.0, 118.8, 123.6 (q, J=273.2 Hz), 125.4 (q, J=3.8 Hz), 128.3, 133.9 (q, J=32.9 Hz), 140.0, 140.6, 199.7. E-116: $^1$H NMR (400 MHz, CDC13); δ 1.15–2.02 (m, 9H), 2.30 (m,1H), 2.93 (m, 3H), 3.48 (s, 3H), 5.71 (s, 1H), 7.71 (2H, m), 8.03 (2H, m).

General Procedure

Trioxane formation by singlet oxygenation. A sulfonation (3-necked) flask was fitted with a gas inlet line, an outlet line with stopcock, and a septum. To this flask was added solid methylene blue (ca. 5 mg) followed by a solution of the starting ketone (1.0 equivalent) in CH$_2$Cl$_2$ (0.01 M). The resulting solution was cooled to −78 ° C. while UHP oxygen passed through a drying column was bubbled (ca. 1 mL/s) through the solution. The reaction mixture was then irradiated with UV light (medium pressure Hg lamp) with continuous O$_2$ bubbling just until t.l.c. analysis showed >95% consumption of starting material. After irradiation, gaseous argon was introduced through the septum, the outlet stopcock was closed, and the gas inlet line was replaced with a stopper. To this reaction mixture, still at −78 ° C., was then added by cannula a −78° C. solution of t-BuMe$_2$SiOTf (1.1 equivalents) in CH$_2$Cl$_2$ (0.50 M). The resulting solution was stirred for 8 h at −78° C. At that time, the reaction was quenched by addition via syringe over 2 min of Et$_3$N (neat, 3.3 equivalents). The mixture was allowed to warm to room temperature (r.t.) slowly over at least 3 h and was then concentrated under reduced pressure to ca. 1 mL total volume.

C$_3$—Fluoromethyl Trioxanes 118

Fluoromethyl ketone Z-115 (281 mg, 1.31 mmol) was treated according to the general procedure (20 mL CH$_2$Cl$_2$, irradiation for 2 h). The crude product was purified by column chromatography (flash gel, 10% EtOAc/hexanes) to give C11α-OMe trioxane α-118 (132 mg, 41%) and C$_{11β}$-OMe trioxane β-118 (17 mg, 5%).

Trioxane α-118: m.p.=80–81° C.; $^1$H NMR (400 MHz, CDCl$_3$) δ 1.15–1.34 (m, 2 H), 1.60–1.75 (m, 7 H), 1.85 (m, 2 H), 2.12 (m, 1 H), 2.22–2.35 (m, 1 H), 3.52 (s, 3 H), 4.25 (d ABq, J d(H—F)=47.2 Hz, ΔVAB=18.7 Hz, J AB=10.0 Hz, 2 H), 4.97(s, 1 H),; $^{13}$C NMR (100 MHz, CDCl$_3$) δ 23.7, 24.9, 25.8, 30.8, 33.0, 35.4, 47.3, 57.2, 83.8 (d, J=181 Hz), 84.2, 103.7 (d, J=19.8 Hz), 104.8.

Trioxane β-118: m.p.=75–76° C.; $^1$H NMR (400 MHz, CDCl$_3$) δ 1.15–1.30 (m, 4 H), 1.42–1.54 (m, 1 H), 1.66–1.75 (m, 4 H), 1.85 (m, 1 H), 2.06 (m, 1 H), 2.34 (m, 2 H), 3.51 (s, 3 H), 4.24 (d ABq, J d(H—F)=46.8 Hz, ΔVAB=15.0 Hz, J AB=10.0 Hz, 2 H), 5.01 (d, J=0.8 Hz, 1 H).; $^{13}$C NMR (100 MHz, CDCl$_3$) δ 23.0, 25.2, 26.2, 31.5, 32.5, 33.2, 45.3, 55.6, 84.2, 84.4 (d, J=181 Hz), 95.5, 102.5 (d, J=20.5 Hz).

(note: The stereochemistry assignment of trioxanes 118 is ambiguous and needs to be confirmed)

C$_3$-Trifluoropropyl Trioxanes 119

Trifluoropropyl ketone Z-116 (105.6 mg, 0.38 mmol) was treated according to the general procedure (irradiation for 2 h). The crude reaction mixture was purified by column chromatography (flash gel, 10% EtOAc/hexanes) to give C$_{11β}$-OMe trioxane β-119 (36 mg, 31%) and C$_{11α}$-OMe trioxane α-119 (3.7 mg, 3%). β-119: $^1$H NMR (400 MHz, CDCl$_3$) δ 1.13–2.03 (m, 14H), 2.14–2.38 (m, 3H), 3.52 (s, 3H), 4.90 (s, 1H); $^{13}$C NMR (100 MHz, CDCl$_3$) δ 23.7, 25.0, 26.5, 27.7 (q, J=29.6 Hz), 30.8, 32.1 (q, J=2.3 Hz), 35.5, 36.9, 47.4, 57.1, 83.8, 104.3, 104.8, 127.0 (q, J=273.8 Hz).

α-119: $^1$H NMR (400 MHz, CDCl$_3$) δ 1.15–1.56 (m, 5H), 1.65 (m, 4H), 1.81–2.01 (m, 4H), 2.21–2.41 (m, 4H), 3.55 (s, 3H), 4.96 (s, 1H); $^{13}$C NMR (100 MHz, CDCl$_3$,) δ 23.1, 25.2, 26.9, 27.8 (q, J=29.8 Hz), 32.17 (q, J=3.0 Hz), 32.4. 33.2, 35.6, 45.3, 56.1, 83.8, 95.8, 103.4.

(Note: CF$_3$- carbon peak is missing, too weak to observe)

C$_3$-(p-Trifluoromethyl)phenyl Trioxanes 120 p-(Trifluoromethyl) phenyl ketone Z-117 (138 mg, 0.423 mmol) was treated according to the general procedure (irradiation for 2 h). The crude reaction mixture was purified by column chromatography (flash gel, 8% EtOAc/hexanes) to give C$_{12β}$-OMe trioxane β-120: m.p.=97–98° C.; $^1$H NMR (400 mHz, CDCl$_3$) δ 1.17–1.81 (m, 9H), 1.83–2.20 (m, 2H), 2.23 (m, 1H), 2.77 (m, 1H), 3.66 (s, 3H), 5.14 (d, 1H, J=1.2 Hz), 7.64 (m, 4H).

α-120: m.p.=137–138° C.; $^1$H NMR (400 MHz, CDCl$_3$) δ 1.59–1.94 (m, 10H), 2.19 (m, 1H), 2.42 (m, 1H), 2.83 (m, 1H), 3.59 (s, 3H), 5.19 (s, 1H), 7.64 (m, 4H).

Synthesis of C$_{12}$-(p-carboxy)benzyloxy Trioxanes MK012

C$_{12}$-(p-carboxy)benzyloxy trioxanes MK012 can be prepared by the following scheme:

Scheme IV

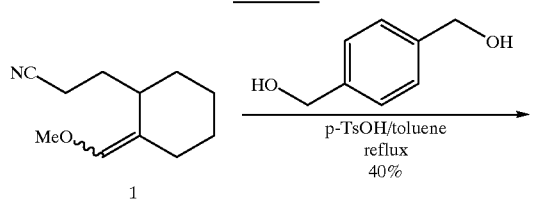

1

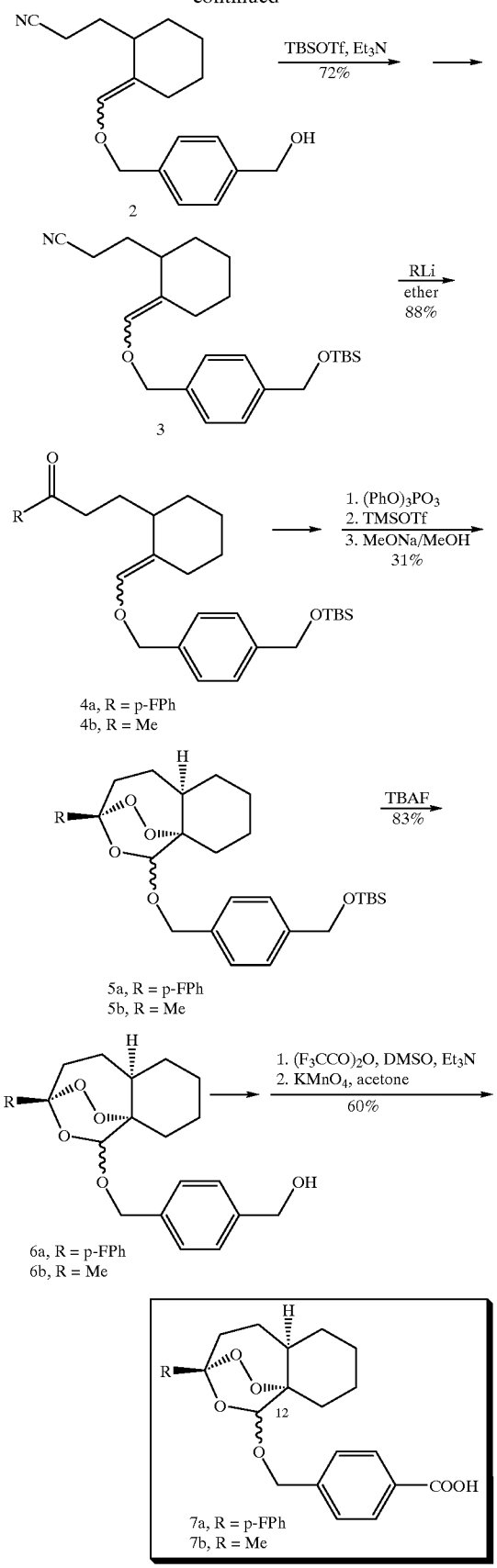

Experimental
(Numbering in the following section refers to Scheme IV.)
p-((tert-Butyldimethylsilyl)oxymethyl)
benzyloxymethylidene-ne-2-(2-cyanoethyl)cyclohexane 3

2-(2-Cyanoethyl)methoxy-methylidene cyclohexane 1 (370 mg, 2.06 mmol) was dissolved in 40 mL of anhydrous toluene. 1,4-Benzenedimethanol (314 mg, 2.27 mmol, 1.1 equiv.) and p-toluenesulfonic acid (4 mg, 0.02 mmol, 0.01 equiv.) were added and the reaction was heated under reflux for 1 hr. Then it was cooled to room temperature and triethylamine (0.5 mL) was added to neutralize the acid. The toluene solution was washed with $H_2O$ (20 mL), aqueous phase was separated and extracted with $CH_2Cl_2$ (2×20 mL). The combined organic phases were dried over anhydrous $MgSO_4$, filtered, and concentrated in vacuo. The crude product was purified by column chromatography on silica gel using 30% ethyl acetate in hexanes to give 235 mg (0.82 mmol 40%) of the (p-hydroxymethyl)benzyl enol ether 2 containing some impurities: $^1$H NMR (400 MHz, $CDCl_3$) δ 7.30–7.37 (m, 4H), 5.98 (d, J=1.6 Hz) and 5.88 (d, J=0.8 Hz)-1H total, 4.66–4.79 (m, 4H), 2.89–2.94 (m) and 2.50 (dt, $J_d$=14.0 Hz, $J_t$=4.0 Hz)-1H total, 2.32–2.47 (m, 1H), 2.04–2.20 (m, 3H), 1.10–2.00 (m, 9H); $^{13}$C NMR (100 MHz, $CDCl_3$) —characteristic peaks: δ 140.7, 140.6, 139.5, 138.6, 137.0, 136.8, 128.0, 127.7, 127.1, 127.0, 120.7, 120.0, 119.0, 118.2, 73.4, 73.3, 64.9, 37.6, 32.7, 32.6, 28.0, 27.5, 26.9, 26.8, 26.4, 22.3, 22.1, 21.6, 15.2, 15.1; IR (KBr, neat) 3446 (broad), 2927, 2245, 1676, 1449, 1132, 812 cm$^{-1}$.

The alcohol 2 (190 mg, 0.67 mmol), obtained in the previous step, was dissolved in methylene chloride (10 mL) and treated with triethylamine (339 ma, 3.35 mmol, 5.0 equiv.) and tert-butyldimethylsilyl trifluoromethane-sulfonate (221 mg, 0.80 mmol, 1.2 equiv.) at 0° C. The reaction was stirred at 0° C. for 15 min and then was poured into cold 10% aqueous $NaHCO_3$ (20 mL). Organic phase was separated and the aqueous phase was extracted with ether (2×10 mL). Combined organic extracts were dried over anhydrous $MgSO_4$, filtered, and concentrated in vacuo. Purification of the crude product by column chromatography on silica gel using 5% ethyl acetate in hexanes afforded 192 mg (0.48 mmol, 72%) of the desired silyl ether 3 as colorless oil: $^1$H NMR (400 MHz, $CDCl_3$) δ 7.25–7.35 (m, 4H), 5.99 (s) and 5.91 (s)-1H total, 4.66–4.79 (m, 4H), 2.94 (dm, J=10.4 Hz) and 2.50 (dt, $J_d$=14.0 Hz, $J_r$=3.6 Hz)-1H total, 2.03–2.25 (m, 2H), 1.78–1.97 (m, 2H), 1.42–1.73 (m, 7H), 1.10–1.30 (m, 1H), 0.95 (s, 9H), 0.11 (s, 6H); $^{13}$C NMR (100 MHz, $CDCl_3$) δ 141.2, 141.1, 139.5, 138.7, 136.2, 136.1, 127.6, 127.4, 126.1, 120.6, 119.9, 118.8, 117.8, 73.4, 64.7, 64.6, 37.6, 32.7, 31.3, 28.0, 27.6, 27.0, 26.9, 26.3, 25.9, 22.4, 22.1, 21.6, 18.4, 15.2, 15.1, −5.3; IR (KBr, neat) 2927, 2855, 2244, 1678, 1462, 1363, 1257, 1121, 1092, 838, 777 cm$^{-1}$; LRMS (CI, $NH_3$, rel intensity) 417 (M+$NH_4$, 100), 400 (M+H$^+$, 35), 399 (M$^+$, 2), 371 (M$^+$-$CH_3OH$, 16), 342 (M$^+$-t-Bu, 12), 285 (M$^+$-TBDMS, 57), 268, 235.

p-((tert-Butyldimethylsilyl)oxymethyl)
benzyloxymethylide-ne2-(1-(p-fluorophenyl)-1-oxopropyl) cyclohexane 4a To a solution of 1-bromo-4-fluorobenzene (109 mg, 0.62 mmol, 1.3 equiv.) in ether (3 mL) at −78° C. was added via syringe t-BuLi (1.7M in pentane, 0.7 mL, 1.20 mmol, 2.5 equiv.) over 1 min. The resulting clear yellow solution was stirred at −78° C. for 30 min. A −78° C. solution of the nitrile 3 (192 mg, 0.48 mmol, 1.0 equiv.) in ether (5 mL) was then added dropwise via cannula. The reaction was stirred at −78° C. for 15 min, then warmed to room temperature and stirred at room temperature for 30 min. The reaction was quenched at 0° C. with dropwise addition of water. The mixture was the diluted with water (10 mL) and ether (20 mL). The organic layer was separated and the aqueous phase was extracted with ether (2×10 mL). Organic extracts were combined, washed with saturated aqueous NaCl, dried over anhydrous $MgSO_4$, filtered and concentrated under reduced pressure. Purification of the crude product by column chromatography on silica gel using 10% ethyl acetate in hexanes afforded the ketone 4a (210 mg, 88%) as mixture of (E)- and (Z)-isomers: $^1$H NMR (400 MHz, $CDCl_3$) δ 7.90 (ddd, J=9.2, 5.2, 2.8 Hz, 2H), 7.22–7.33 (m, 4H), 7.04–7.14 (dm, J=16.0 Hz, 2H), 5.96 (d, J=2.0 Hz) and 5.84 (s)-1H total, 4.68–4.74 (m, 2H), 4.64 (ABq, $J_{AB}$=12.4 Hz, $\Delta v_{AB}$=32.1 Hz, 2H), 2.95–3.01 (m, 1H), 2.84–2.92 (m, 1H), 2.78–2.83 (m, 1H), 2.39 (dt, Jd=14.0 Hz, $J_t$=4.4 Hz) and 1.81 (dt, $J_{d=}$13.6 Hz, $J_t$=2.8 Hz)-1H total, 1.94–2.03 (m, 2H), 1.48–1.78 (m, 7H), 0.94 (s) and 0.93 (s)-9H total, 010 (s) and 0.09 (s)-6H total; $^{13}$C NMR (100 MHz, $CDCl_3$) δ 199.3, 199.0, 165.6 (d $J_{C-F}$=252.8 Hz), 165.4 (d $J_{C-F}$=252.8 Hz), 141.0, 140.9, 138.8, 138.0, 136.5, 136.4, 133.6 (d $J_{C-F}$=2.8 Hz), 133.5 (d $J_{C-F}$=4.4 Hz), 130.6, 130.5, 127.3 (d $J_{C-F}$=5.3 Hz), 126.0, 120.9, 119.8, 115.5 (d $J_{C-F}$=21.2 Hz), 115.4 (d $J_{C-F}$=22.0 Hz), 73.3, 73.2, 64.7, 38.6, 36.9, 36.7, 33.6, 32.8, 31.8, 28.3, 27.2, 26.5, 26.0, 25.9, 25.8, 22.9, 22.8, 21.6, 18.4–5.3; IR (KBr, neat) 2927, 1688, 1598, 1506, 1462, 1409, 1365, 1233, 1156, 837, 777 $cm^{-1}$; LRMS (CI, $NH_3$, rel intensity) 514 ($M+NH_4^+$, 9), 497 ($M+H^+$, 3), 439 (M+-t-Bu, 1), 365 ($M^+$-TBDMSO, 1), 301 (10), 278 (53), 261 (41), 252 (100), 235 (53); HRMS (CI, NH3) m/z calcd for $C_{30}H_{45}NO_3FSi$ ($M+NH_4+$) 514.3153, found 514.3156.

TBDMS-Protected Trioxanes (α)-Sa and (β)-5a

A flame-dried three-necked round-bottomed flask equipped with gas inlet, gas outlet, and a septum was charged with a solution of if triphenylphosphite (248 mg, 0.80 mmol, 2 equiv.) in dry methylene chloride (30 mL). Ozone was bubbled through this mixture at −78° C. until the blue color persisted. The excess of ozone was removed by bubbling dry oxygen gas through the solution as monitored by the disappearance of the blue color. The mixture was then kept at −78° C. A −78° C. solution of (E, Z)-mixture of ketones 4a (200 mg, 0.40 mmol, 1 equiv.) in methylene chloride (10 mL) was added via cannula and the reaction was stirred at −78° C. for 15 min. Trimethylsilyl trifluoromethanesulfonate (80, µL, 0.44 mmol, 1.1 equiv.) in methylene chloride (3 mL) was pre-cooled to −78?C. and added to the reaction mixture. The latter turned bright-yellow and was stirred for additional 15–30 min at −78° C. The reaction was quenched by dropwise addition of 25% w/v sodium methoxide solution in methanol (0.5 mL) and water (2 mL) at −78° C. Then it was warmed up to room temperature and diluted with water and methylene chloride. Organic layer was separated and the aqueous phase was extracted twice with methylene chloride. Combined organic extracts were washed with brine, dried over $MgSO_4$, filtered, and concentrated under reduced pressure. Purification of the crude product by column chromatography on silica gel using 5% ethyl acetate in hexanes afforded trioxanes (α)-5a (42 mg, 0.08 mmol, 20%) and (β)-5a (23 mg, 0.04 mmol, 11%) as colorless oils.

(α)-5a: $^1$H NMR (400 MHz, $CDCl_3$) δ 7.51–7.56 (m, 2H), 7.33 (ABq, $J_{AB}$=8.0 Hz, $\Delta v_{AB}$=24.3 Hz, 4H), 7.04 (tt, J=8.8, 2.0 Hz, 2H), 5.26 (s, 1H), 4.87 (ABq, $J_{AB}$=12.0 Hz, $\Delta v_{AB}$=79.5 Hz, 2H), 4.75 (s, 2H), 2.83 (ddd, J=13.2, 10.8, 4.0 Hz, 1H), 2.46 (dm, J=13.2 Hz, 1H), 2.25 (ddd, J=14.8, 4.4, 2.0 Hz, 1H), 1.67–1.83 (m, 4H), 1.53–1.63 (m, 4H), 1.18 (tt, J=13.2, 4.0 Hz, 1H), 1.08 (m, 1H), 0.94 (s, 9H), 0.09 (s, 6H); $^{13}$C NMR (100 MHz, $CDCl_3$) δ 162.9 (d, $J_{C-F}$=246.1 Hz), 141.2, 136.5 (d, $J_{C-F}$=3.4 Hz), 135.9, 128.4, 127.5 (d, $J_{C-F}$=8.2 Hz), 126.1, 114.8 (d, $J_{C-F}$=21.4 Hz), 103.7, 93.2, 83.7, 69.2, 64.8, 45.5, 37.6, 33.4, 32.4, 27.1, 25.9, 25.1, 22.7, 18.4, −5.2; LRMS (CI, $NH_3$, rel intensity) 546 ($M+NH_4^+$, 9), 298 (34), 279 (10), 266 (10), 252 (50), 249 (100), 166 (51).

(β)-5a: $^1$H NMR (400 MHz, $CDCl_3$) δ 7.49–7.54 (m, 2H), 7.36 (ABq, $J_{AB}$=8.4 Hz, $\Delta v_{AB}$=14.5 Hz, 4H), 7.01–7.07 (m, 2H), 5.33 (d, J=1.0 Hz, 1H), 4.89 (ABq, $J_{AB}$=12.0 Hz, $\Delta v_{AB}$=142.3 Hz, 2H), 4.76 (s, 2H), 2.79 (ddd, J=14.8, 13.2, 3.6 Hz, 1H), 2.30 (ddd, J=14.4, 4.4, 3.2 Hz, 1H), 1.99–2.10 (m, 1H), 1.72–1.87 (m, 4H), 1.62–1.70 (m, 4H), 1.28 (td, $J_t$=13.6 Hz, Jd=4.4 Hz, 1H), 1.15–1.24 (m, 1H), 0.95 (s, 9H), 0.11 (s, 6H3); $^{13}$C NMR (100 MHz, $CDCl_3$) δ 162.9 (d, $J_{C-F}$=246.0 Hz), 141.1, 136.7 (d, $J_{C-F}$=3.3 Hz), 135.9, 127.9, 127.4 (d, $J_{C-F}$=8.2 Hz), 126.1, 115.1 (d, $J_{C-F}$=21.9 Hz), 104.8, 102.6, 83.9, 71.1, 64.8, 47.5, 39.1, 35.5, 30.9, 26.8, 26.0, 25.0, 24.0, 18.4, −5.3; LRMS (CI, $NH_3$, rel intensity) 546 ($M+NH_4^+$, 2), 500 (1), 298 (27), 266 (12), 252 (21), 249 (100), 166 (38); HRMS (CI, $NH_3$) m/z calcd for $C_{30}H_{45}NO_5FSi$ ($M+NH_4^+$) 546.3051, found 546.3061.

(p-hydroxymethyl)benzyloxy Trioxane (α)-6a

Trioxane (α)-5a (42 mg, 79 µmol) was dissolved in THF (2 mL) and treated with tetrabutylammonium fluoride (TBAF, 1.0 M solution in THF, 95 µL, 95, µmol, 1.2 equiv.) at 0° C. Formation of a white precipitate was observed. Reaction was warmed up to room temperature and was stirred at that temperature overnight. Then it was diluted with $H_2O$ (2 mL), organic layer was separated, and the aqueous phase was extracted with methylene chloride (2×5 mL). Combined organic extracts were dried over anhydrous $MgSO_4$, filtered, and concentrated in vacuo. Purification of the residue by column chromatography on silica gel using 40% ethyl acetate in hexanes afforded trioxane (α)-6a (28 mg, 68 µmol, 86%) as a white solid: mp=128–129° C.; $^1$H NMR (400 MHz, $CDCl_3$) δ 7.51–7.56 (m, 2H), 7.37 (ABq, $J_{AB}$=8.0 Hz, AVAB=19.2 Hz, 4H), 7.01–7.07 (m, 2H), 5.28 (s, 1H), 4.88 (ABq, JAB=12.4 Hz, $\Delta v_{AB}$=85.1 Hz, 2H), 4.70 (s, 2H), 2.83 (ddd, J=14.4, 13.6, 4.0 Hz, 1H), 2.47 (dm, J=12.8 Hz, 1H), 2.25 (ddd, J=14.8, 4.8, 2.8 Hz, 1H), 1.55–1.85 (m, 6H), 1.07–1.28 (m, 3H), 0.98 (tt, J=13.6, 3.2 Hz, 1H); $^{13}$C NMR (100 MHz, $CDCl_3$) δ 162.9 (d, $J_{C-F}$=246.1 Hz), 140.5, 136.9, 136.5 (d, $J_{C-F}$=2.2 Hz), 128.5, 127.4 (d, $J_{C-F}$=8.2 Hz), 127.0, 115.1 (d, $J_{C-F}$=21.4 Hz), 103.8, 93.4, 83.7, 69.1, 65.1, 45.5, 37.6, 33.4, 32.4, 27.1, 25.1, 22.8; LRMS (CI, $NH_3$, rel intensity) 432 ($M+NH_4^+$, 1), 348 (2), 296 (3), 279 (13), 250 (100), 184 (31), 138 (33), 125 (15).

(p-hydroxymethyl)benzyloxy Trioxane (β)-6a

Trioxane (β)-5a (23 mg, 44 µmol) was deprotected in the same manner as above. Purification of the crude product by column chromatography on silica gel using 25% ethyl acetate in hexanes afforded 14 mg (35 µmol, 80%) of the trioxane (β)-6a as a sticky foamy solid: $^1$H NMR (400 MHz, $CDCl_3$) δ 7.49–7.52 (m, 2H), 7.40 (ABq, $J_{AB}$=8.4 Hz, AVAB=9.1 Hz, 4H), 7.01–7.07 (m, 2H), 5.33 (unresolved d, 1H), 4.91 (ABq, $J_{AB}$=12.0 Hz, $\Delta v_{AB}$=145.9 Hz, 2H), 4.72 (s, 2H), 2.79 (ddd, J=14.4, 13.6, 3.6 Hz, 1H), 2.31 (ddd, J=14.8, 4.4, 3.2 HZ, 1H), 1.99–2.10 (m, 2H), 1.62–1.88 (m, 7H), 1.29 (td, $J_t$=13.6 HZ, $J_d$=5.2 Hz, 1H), 1.18 2–1.24 (m, 1H); $^{13}$C NMR (100 MHz, $CDCl_3$) δ 162.9 (d, $J_{C-F}$=246.5 Hz), 140.5, 136.8, 136.7 (unresolved d), 128.2, 127.3 (d, $J_{C-F}$=8.2 Hz), 127.1, 115.1 (d, $J_{C-F}$=21.8 Hz), 104.8, 102.6, 83.9, 71.0, 65.1, 47.5, 39.1, 35.5, 30.9, 26.8, 25.0, 24.0; LRMS (CI, $NH_3$, rel intensity) 432 ($M+NH_4^+$, 5), 415 ($M+H^+$, 1), 382 ($M^+$-$O_2$, 1), 277 (11), 266 (11), 249 (100), 184 (22).

(p-Carboxy)benzyloxy Trioxane (α)-7a

A 10 mL flame-dried round-bottomed flask was charged with a solution of DMSO (8, µl, 110 µmol, 2.0 equiv.) in methylene chloride (1 mL). It was cooled to −78° C. and trifluoroacetic anhydride (13 μl, 83 μmol, 1.5 equiv.) was added via syringe. The reaction was stirred at −78° C. for 20 min while the formation of a white precipitate was observed. At that point a −78° C. solution of the trioxane (α)-6a (23 mg, 55 μmol) in methylene chloride (2 mL) was added via cannula. The reaction was stirred at −78° C. for 1 hr. Triethylamine (100 AL) was added and the reaction was warmed to ca. 0° C. and was further quenched with 1.5 mL of saturated aqueous NaHCO₃ at that temperature. The organic soluble materials were taken up to ether, the etherial extracts were dried over anhydrous MgSO₄, filtered, and concentrated in vacuo. The crude product was fractionated on a short Floresil® column using 10% ethyl acetate in hexanes.

The fractions containing the corresponding aldehyde-trioxane were combined, the solvent was evaporated, and the residue was dissolved in acetone (1 mL). Potassium permanganate (15 mg, 96 μmol, 2.0 equiv.) was added at 0° C. and the reaction was stirred at 0° C. for 15 min and then at room temperature for 3 hours. The excess of KMnO₄ was reduced over 30 min with isopropyl alcohol (3 mL). The reaction was filtered through a plug of silica gel and the MnO₂ precipitate was thoroughly washed with methanol. The combined filtrate and washings were concentrated in vacuo and the residue was loaded on a Floresil® column. The column was eluted with 50–70% ethyl acetate in hexanes to remove the less polar impurities. Then the pure carboxylic acid was washed out of the column with methanol. Evaporation of the solvent in vacuo provided the trioxane (α)-7a (14 mg, 33 μmol, 60%) as a white solid: $^1$H NMR (400 MHZ, CD₃OD) δ 7.91–7.94 (m, 2H), 7.52–7.57 (m, 2H), 7.40 (br s, 1H), 7.38 (br s, 1H), 7.08 (td, $J_t$=8.8 HZ, $J_d$=2.4 HZ, 2H), 5.38 (s, 1H), 4.88 (ABq, $J_{AB}$=12.4 HZ, $\Delta v_{AB}$ 56.7 HZ, 2H), 2.80 (ddd, J=14.4, 13.2, 3.6 HZ, 1H), 2.35–2.40 (m, 1H), 2.20 (ddd, J=14.4, 4.4, 2.4 Hz, 1H), 1.77–1.82 (m, 1H), 1.66–1.75 (m, 2H), 1.56–1.64 (m, 2H), 1.05–1.28 (m, SH); $^{13}$C NMR (100 MHz, CD₃OD) δ 175.3, 164.5 (d, $J_{C-F}$=245.2 Hz), 14i.2, 138.9, 138.4 (d, JC—F=3.0 Hz), 130.6, 129.0 (d, $J_{C-F}$=9.9 Hz), 116.1 (d, $J_{C-F}$=21.3 Hz), 105.2, 95.4, 85.0, 70.7, 47.1, 39.0, 34.7, 33.6, 28.3, 26.5, 24.0.

(p-Carboxy)benzyloxy Trioxane (β)-7a

The trioxane (β)-6a (12 mg, 29, μmol) was oxidized in the same manner as above to give 8 mg (19 μmol, 65%) of the trioxane (β)-7a as a white solid: 1H NMR (400 MHz, CD₃OD) δ 7.94 (t, J=8.8 Hz, 2H), 7.49–7.54 (m, 2H), 7.44 (br s, 1H), 7.42 (br s, 1H), 7.08 (td, $J_t$=8.8 Hz, $J_d$=2.4 Hz, 2H), 5.33 (d, J=1.2 Hz, 1H), 4.94 (ABq, $J_{AB}$=12.0 Hz, $\Delta v_{AB}$ 115.4 Hz, 2H), 2.78 (ddd, J=14.4, 13.2, 3.6 Hz, 1H), 2.26 (ddd, J=14.4, 4.4, 3.2 Hz, 1H), 1.98–2.18 (m, 2H), 1.62–1.85 (m, SH), 1.20–1.32 (m, 4H); $^{13}$C NMR (100 MHz, CD₃OD) δ 175.4, 164.5 (d, $J_{C-F}$=248.5 Hz), 141.1, 139.0, 138.5 (d, $J_{C-F}$=3.0 Hz), 130.6, 130.5, 128.9 (d, $J_{C-F}$=9.9 Hz), 116.0 (d, $J_{C-F}$=21.3 Hz), 106.3, 104.5, 85.0, 72.5, 40.3 36.7, 32.2, 28.2, 26.3, 25.2.

Carboxylic Acid Analogs of Artemisinin

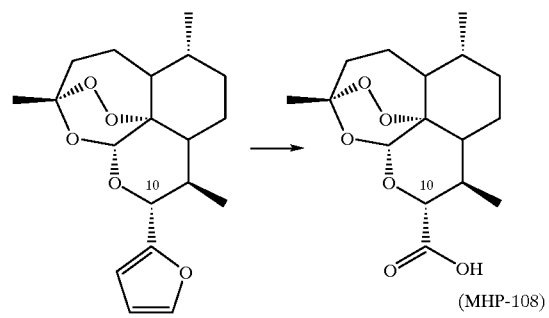

10α-Carboxy-10-deoxoartemisinin (MHP-108)

10α-(2'-Furyl)-10-deoxoartemisinin (160 mg, 0.478 mmol) was dissolved in acetonitrile (5 mL), carbon tetrachloride (3 mL), and distilled water (3 mL). To the heterogeneous mixture was added sodium periodate (1.023 g, 4.78 mmol) and then a catalytic amount of ruthenium dioxide (~6 ma, 0.048 mmol). The reaction mixture was stirred at room temperature and a white precipitate slowly formed. After about 8 hours, the reaction was diluted with dichloromethane and water. The layers were separated and the aqueous layer was extracted with dichloromethane (3×3 mL). The combined organic layer was filtered through a short plug of Celite to remove the black solid. The filtrate was dried over magnesium sulfate, concentrated, and chromatographed on Florisil (5% methanol in dichloromethane) to give the carboxylic acid MHP-108 (149 ma, 0.478 mmol, 100% yield) as a white solid. Mp: 146–149° C.

$$[\alpha]\frac{25}{D} = +79.4(c = 0.70, CHCl_3).$$

$^1$H NMR (CDCl³, 400 MHz) 6: 5.36 (s, 1 H), 3.90 (d,=10.8 Hz, 1 H), 2.48–2.56 (m, 1H), 2.31 (dt, J=14.0, 3.6 Hz, 1 H), 2.01–2.07 (m, 1 H), 1.87–1.94 (m, 1 H), 1.70–1.76 (m, 1 H), 1.38–1.56 (m, 4 H), 1.38 (s, 3 H), 1.18–1.30 (m, 1 H), 0.98–1.12 (m, 1 H), 0.97 (d, J=6.0 Hz, 3 H), 0.86 (d, J=6.8 Hz, 3 H). $^{13}$C NMR (CDCl₃, 100 MHz) δ: 177.6, 105.6, 93.5, 82.1, 79.1, 53.6, 47.4, 38.5, 37.5, 35.4, 32.2, 26.1, 26.0, 22.6, 20.9, 14.2. IR (CHCl₃): 3443, 2927, 1603, 1444, 1379, 1195, 1129, 1087, 1043, 912, 878, 732 cm⁻¹. HRMS (CI, NH₃): m/z calcd for C16H24O6 (M+) 312.1811, found 312.1818. In vitro antimalarial assay: IC₅₀=570 nM. (Artemisinin IC₅₀=10 nM).

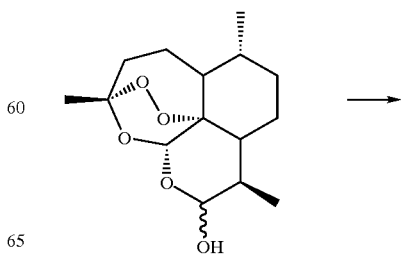

-continued

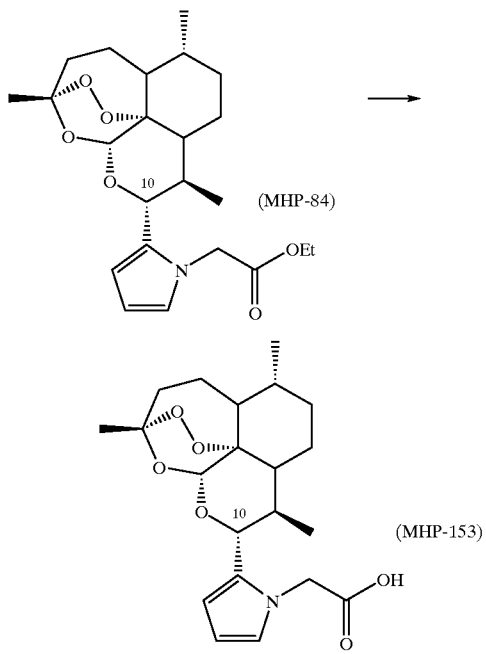

10a-(1'-(Ethoxycarbonylmethyl)pycrol-2'-yl)-10-deoxoartemisinin (MHP-84)

Dihydroartemisinin (53 ma, 0.186 mmol) and N-(ethoxycarbonylmethyl)pyrrole 143 ma, 0.932 mmol) were dissolved in dry dichloromethane 3 mL) and the solution was cooled to −78° C. Boron trifluoride diethyl etherate (32 mg, 28, μL, 0.224 mmol) was added slowly by syringe. The reaction was stirred for 30 min at −78° C. and then the temperature was raised to −50° C. After stirring overnight at −50° C., the reaction was quenched with distilled water (5 mL). The aqueous phase was separated and extracted with dichloromethane (5 mL×2). The combined organic solution was dried over magnesium sulfate and concentrated under reduced pressure. The resulting oil was purified by column chromatography on Florisil (10% ethyl acetate in hexanes) to provide the product MHP-84 (50 mg, 0.119 mmol, 64% yield) as a white foam.

$$[\alpha]\frac{25}{D} = +97.2(c = 1.61, CHCl_3).$$

HPLC: 3:97 ethanol:hexanes, 3 mL/min, 235 nm, $R_t$=8.0 min. $^1$H NMR (CDCl$_3$, 400 MHz) 6: 6.59 (dd, J=1.6, 2.8 Hz, 1 H), 6.07 (dd, J=2.8, 3.6 Hz, 1 H), 5.99 (dd, J=1.6, 3.6 Hz, 1 H), 5.44 (d, J=18.0 Hz, 1 H), 5.36 (s, 1 H), 4.83 (d, J=18.0 Hz, 1 H), 4.52 (d, J=11.2 Hz, 1 H), 4.15–4.27 (m, 2 H), 2.55–2.64 (m, 1 H), 2.39 (ddd, J=4.0, 13.2, 14.4 Hz, 1 H), 2.03 (ddd, J=2.8, 4.8, 14.4 Hz, 1 H), 1.85–1.92 (m, 1 H), 1.69–1.76 (m, 2 H), 1.40 (s, 3 H), 1.26 (t, J=7.0 Hz, 3 H), 1.0–1.6 (m, 6 H), 0.97 (d, J=6.4 Hz, 3 H), 0.61 (d, J=7.2 Hz, 3 H). $^{13}$C NMR (100 MHz, CDCl$_3$) δ: 170.0, 129.7, 124.0, 109.5, 107.4, 104.3, 91.8, 80.6, 72.8, 61.1, 51.8, 48.9, 45.8, 37.4, 36.2, 34.1, 31.4, 26.0, 24.8, 20.9, 20.3, 14.3, 14.2. IR (neat): 2928, 2872, 1753, 1376, 1300, 1197, 1126, 1099, 1042, 880, 712 cm$^{-1}$. HRMS (EI): m/z calcd for C$_{23}$H$_{33}$NO$_6$ (M$^+$) 419.2308, found 419.2300. In vivo antimalarial assay: IC$_{50}$=9.1 nM.

10a-(1'-(Carboxymethyl)pyrrol-2'-yl)-10-deoxoartemisinin (MHP-153)

10a-(1'-(Ethoxycarbonylmethyl)pyrrol-2'-yl)-10-deoxoartemisinin (MHP-84, 28 mg, 0.067 mmol) was dissolved in tetrahydrofuran (5 mL). Distilled water (1 mL) and then lithium hydroxide monohydrate (14 mg, 0.333 mmol) were added. The reaction was stirred for 3 hours at room temperature. The reaction was quenched with saturated aqueous ammonium chloride (5 mL) and diluted with diethyl ether (5 mL). The aqueous layer was separated and extracted with dichloromethane (3×5 mL). The combined organic layer was dried over magnesium sulfate, concentrated, and chromatographed on Florisil to give the carboxylic acid MHP-153 (23 mg, 0.059 mmol, 88% yield) as a white solid. Mp: 124–125° C.

$$[\alpha]\frac{25}{D} = +40.5(c = 1.12, MeOH).$$

$^1$H NMR (CD$_3$OD, 400 MHz) δ: 6.59 (t, J=1.8 Hz, 1 H), 6.05 (dd, J=3.6, 2.0 Hz, 1 H), 5.96 (t, J=3.0 Hz, 1 H), 5.45 (s, 1 H), 4.67 (d, J=17.2 Hz, 1 H), 4.57 (d, J=17.2 Hz, 1 H), 4.55 (d, J=10.8 Hz, 1 H), 2.72–2.81 (m, 1 H), 2.30 (dt, J=4.0, 14.4 Hz, 1 H), 1.98–2.20 (m, 1 H), 1.84–1.92 (m, 1 H), 1.30 (s, 3 H), 1.0–1.7 (m, 8 H), 0.95 (d, J=6.0 Hz, 3 H), 0.72 (d, J=7.2 Hz, 3 H). $^{13}$C NMR (CD$_3$OD, 100 MHz) δ: 177.1, 131.5, 124.5, 109.2, 107.6, 105.6, 93.6, 82.1, 72.0, 53.7, 52.5, 47.7, 38.7, 37.6, 35.6, 32.4, 26.2, 22.3, 20.9, 15.4. IR (neat): 3752, 3406, 2926, 1604, 1396, 1310, 1125, 1039cm$^{-1}$. Anal. calcd for C$_{21}$H$_{29}$NO$_6$: C 64.43, H 7.47, N 3.58, found: C 64.48, H 7.46, N 3.59. In vitro antimalarial assay: IC$_{50}$=36 nM.

Scheme V

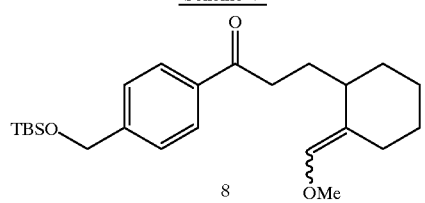

8

1. (PhO)$_3$PO$_3$
2. TMSOTf
3. MeONa/MeOH

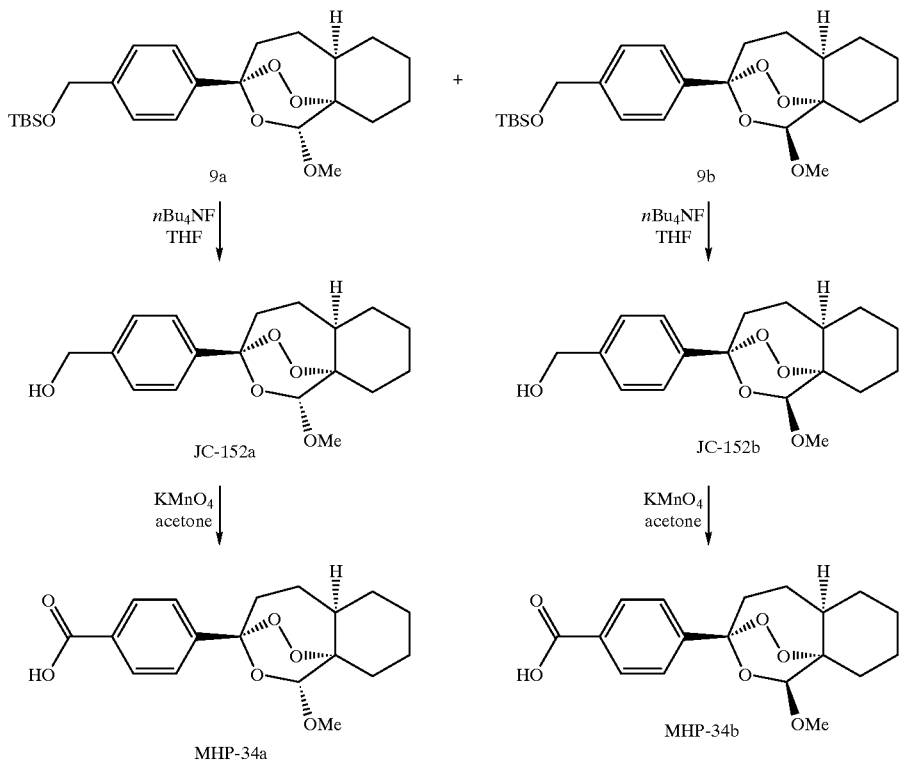

3-(4'-(t-Butyldimethlysilyloxymethyl)phenyl) Trioxanes 9ab

A preferred method for the conversion of compound 8 to compound 9 is shown in Scheme V and is carried out as follows:

A three-necked 1 L flask was equipped with a gas dispersion bubbler inlet, an ozone resistant septa, and a gas outlet. Dry dichloromethane (500 mL) was added to the flask under an argon atmosphere. The solution was cooled to −78° C. An ozone/oxygen gas mixture was bubbled through the solution until saturated, as evidenced by a deep blue color. While continuing oxone addition, triphenylphosphite (13.0 mL, 15.4 g, 49.7 mmol) in dry dichloromethane (37 mL) was added by syringe pump at such a rate that the blue color persisted using a syringe needle with its tip below the level of the solution. Upon completion of the phosphite addition, the reaction mixture was purged of excess ozone by bubbling argon through the solution for about one hour, producing a colorless solution of triphenylphosphite ozonide. The enol ether 8 (10.0 g, 24.8 mmol) was then dissolved in dry dichloromethane (100 mL) and the solution was cooled to −78° C. This solution was then transferred slowly by cannula to the phosphite ozonide solution. After one half hour at −78° C., a solution of trimethylsilyl triflate (4.94 mL, 6.07 g, 27.3 mmol) in dry dichloromethane (100 mL), also at −20 78° C. was transferred slowly to the reaction by cannula. The reaction was then stirred at −78° C. for about 30 minutes. Sodium methoxide (25% in methanol, 11.3 mL, 10.7 g, 49.7 mmol) was added to quench the Lewis acid. The solution was warmed to room temperature and diluted with aqueous sodium bicarbonate. The aqueous phase was separated and extracted with dichloromethane. The combined organic phase was concentrated under reduced pressure and chromatographed over Florisil (1% ethyl acetate in hexanes) to provide the separated isomers 9a and 9b.

3-(4'-Carboxyphenyl)-12α-methoxy Trioxane (MHP-34a)

The 3-(4'-(hydroxymethyl)phenyl)-12α-methoxy trioxane (JC-152a, 40 mg, 0.125 mmol) was dissolved in dry acetone (2 mL). Potassium permanganate (40 mg, 2.50 mmol) was added and the purple solution was stirred at room temperature for 8 hours. Isopropanol was added to the solution and it was stirred overnight. The reaction was filtered through fine filter paper using a Buchner funnel. The filtrate was concentrated under vacuum to give a white solid that was chromatographed through Florisil (5% methanol in dichloromethane) to give the acid (31 mg, 72% yield) as a white solid. Mp: 202° C. (dec). $^1$H NMR (CD$_3$OD, 400 MHz) δ: 7.92 (d, J 8.4 Hz, 2 H), 7.51 (d, J=8.4 Hz, 2 H), 5.26 (s, 1 H), 3.56 (s, 3 H), 2.80 (ddd, J=14.4, 12.8, 3.6 Hz, 1 H), 2.26–2.34 (m, 1 H), 2.18 (ddd, J=14.4, 4.4, 2.4 Hz, 1 H), 1.82–1.89 (m, 1 H), 1.58–1.76 (m, 5 H), 1.24–1.37 (m, 3 H), 1.07–1.15 (m, 1 H). $^{13}$C NMR (CD$_3$OD, 100 MHz) o: 174.9, 144.4, 138.8, 130.5, 126.0, 105.4, 97.6, 85.1, 56.3, 50.0, 47.0, 39.1, 34.7, 33.6, 28.4, 26.6, 24.3, 24.1. IR (MeOH): 3382, 2927, 1595, 1556, 1409, 1100, 1043, 1012, 784 cm$^{-1}$. In vitro antimalarial assay: IC$_{50}$=1020 nM. In vivo antimalarial assay: subcutaneous, ED$_{50}$=19.5, ED$_{90}$=92; oral, ED$_{50}$=9.5, ED$_{90}$=46 mg/kg/day×4.

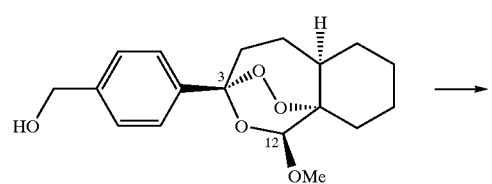

-continued

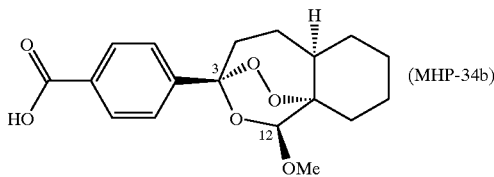
(MHP-34b)

3-(4'-Carboxyphenyl)-12β-methoxy Trioxane (MHP-34b)

The 3-(4'-(hydroxymethyl)phenyl)-12β-methoxy trioxane (JC-152b, 35 mg, 0.109 mmol) was dissolved in acetone (5 mL) and potassium permanganate (172 mg, 1.09 mmol) was added. The purple solution was stirred for 8 hours at room temperature and then isopropanol (5 mL) was added. After 12 hours, the brown suspension was filtered, and washed with additional isopropanol (20 mL). The filtrate was concentrated to a white solid which was chromatographed on Florisil (5% methanol in dichloromethane) and then recrystallized from methanol to provide the carboxylic acid MHP-34b (32 mg, 0.096 mmol, 88% yield) as a white solid. Mp: 195° C. (dec). $^1$H NMR (CD$_3$OD, 400 MHz) δ: 7.96 (d, J=8.0 Hz, 2 H), 7.52 (d, J=8.0 Hz, 2 H), 5.13 (s, 1 H), 3.65 (s, 3 H), 2.78 (dt, J=3.6, 14.0 Hz, 1 H), 2.24 (d, J=14.4, 3.8 Hz, 1 H), 1.85–2.00 (m, 2 H), 1.55–1.79 (m, 7 H), 1.14–1.28 (m, 2 H). IR (MeOH): 3386, 2930, 1594, 1409, 1100, 1043, 786 cm$^{-1}$. In vitro antimalarial assay: IC$_{50}$=150 nM.

Antimalarial Activity

The protozoan *Plasmodium falciparum* is a causative agent of malaria, the single most critical infectious disease of mankind. The in vitro antimalarial activity of the C$_3$-substituted trioxanes was determined according to the method described in Posner et al. (13). The in vivo antimalarial activity was determined as described in Peters et al. (14).

Tables 1 and 2 present a tabulation of a number of compounds which have been synthesized along with the IC$_{50}$ (in nM).

TABLE 1

Antimalarial Activity of C$_3$-Aryl C$_{12}$- Methoxy Trioxanes

| entry | Ar | trioxane | C$_{12}$-OMe | nM |
|---|---|---|---|---|
| 1 | biphenyl | 8a<br>8b | α<br>β | 76[e]<br>68[e] |
| 2 | 4-F-phenyl | 9a<br>9b | α<br>β | 65[e]<br>30[e] |
| 3 | 4-F-2-Me-phenyl | 10a<br>10b | α<br>β | 99[e]<br>34[e] |
| 4 | 4-MeO-phenyl | 11 | 1,2 | >2500[e] |
| 5 | 4-HOCH$_2$-phenyl | 12a<br>12b | α<br>β | 78[e]<br>15[e] |
| 6 | 2-furyl | 13 | α[1] | 600[e] |
| 7 | 2-thienyl | 14a<br>14b | α<br>β | |

TABLE 1-continued

Antimalarial Activity of $C_3$-Aryl $C_{12}$- Methoxy Trioxanes

| entry | Ar | trioxane | $C_{12}$-OMe | nM |
|---|---|---|---|---|
| 8 | quinoline | 15a<br>15b | α<br>β | |
| 9 | phenyl | 16a<br>16b | α<br>β | 100[e]<br>38[e] |

[e]Expansion data (quadruplicate measurements resulting in highly accurate data).
[s]Survey data (one measurement).
[1]Only one trioxane product formed.
[2]Relative stereochemistry at all positions is ambiguous.

TABLE 2

Antimalarial Activity of $C_3$-Substituted $C_{12}$-Methoxy Trioxanes

| entry | R | trioxane | $C_{12}$—OMe | nM |
|---|---|---|---|---|
| 1 | FH$_2$C— | 118a<br>118b | α<br>β | 320[e]<br>160[e] |
| 2 | CF$_3$CH$_2$CH$_2$— | 119a<br>119b | α<br>β | 84[e] |
| 3 | F$_3$C—phenyl— | 120a<br>120b | α<br>β | 39[e]<br>53[e] |
| 4 | H$_3$C— | 121a<br>121b | α<br>β | 960[e] |

[e]Expansion data (quadruplicate measurements resulting in highly accurate data).
[s]Survey data (one measurement).

It is particularly noted that in contrast to Artemisinin analogs (10), branched $C_3$ substituents in the structurally simplified trioxanes of the present invention can have increased potency, the potency of the $C_3$-$(CH_3)_2CHCH_2CH_2$ analog being increased by a factor of 5 over the $C_3$ methyl analog.

$C_3$-p-fluorophenyl $C_{12}$-(carboxy)benzyloxy trioxane exhibited $IC_{50}$'s of 47 nM and 40 nM for the 12α and 12β forms, respectively.

Activity Against *Toxoplasma gondii*

*Toxoplasma gondii* is the causative agent of cerebral toxoplasmic encephalitis, an AIDS-related opportunistic infection. The biological activity of the compounds of the present invention can be measured against *Toxoplasma gondii* cultured in L929 cells.

More specifically, the cytotoxicity of the compounds can be tested in L929 cells by measuring the viability and replication of exposed cells. The cytotoxicity of the compound to the cultured cells can be measured using the MTT assay (Promega kit), according to the procedure of Carmichael et al. (15). MTT is an abbreviation for [3-(4,5-dimethylthiazol-2-yl)-2,5-dephenyltetrazolium bromide].

The inhibitory activity of the compounds can be tested by measuring the intracellular replication of *T. gondii* in infected L929 cells. The inhibition of the intracellular replication of *T. gondii* can be determined using the uracil incorporation assay (16).

While the invention has been described in connection with what is presently considered to be the most practical and preferred embodiments, it is to be understood that the invention is not to be limited to the disclosed embodiments, but on the contrary is intended to cover various modifications and equivalent arrangements included within the spirit and scope of the appended claims, including other anti-infective uses.

The following scientific articles and references have been cited throughout this application and the entire contents of each is hereby incorporated by reference.

REFERENCES

1. Jing-Ming, J., et al., *Acta Chim. Sinica* 37:129 (1979).
2. Schmid, G., et al., *J. Am. Chem. Soc.* 105:624 (1983).
3. Qinghaosu Antimalaria Coordinating Research Group, *Chinese Med. J.* 92:811 (1979).
4. Jiang, J.-B., et al., *Lancet* 2:285 (1982).
5. Bruce-Chwatt, L. J., *Brit. Med. J.* 284:767 (1982).
6. Luo, X. D., et al., *Med. Res. Rev.* 7:29–52 (1987).
7. Klayman, D. L., *Science* 228:1049–1054 (1985).
8. Koch, H., *Pharm. Int.* 2:184–185 (1981).
9. Posner et al. *Heteroatom Chemistry* 6:105–115 (1995)
10. Avery et al., *J. Med. Chem.* 39:2900–2906 (1996)
11. Kamchonwongpaisan et al., *Am. J. Trop. Med. Hyg.* 56: 7–12 (1997).
12. Posner et al. *J. Am. Chem. Soc.* 118: 3537–3538 (1996).
13. Posner et al. *Tetrahedron* 53:37–50 (1997).
14. Peters et al. Ann. Trop. Med. Parasitl. 87:1–7 (1993).
15. Carmichael, J., et al., *Cancer Res.* 47:936–942 (1987).

16. Fraser, D. C., et al., *Biochem. Biophys. Res. Comm.* 135:886–893 (1986).
17. Looareesuwan, S., et al. *Am. J Trop. Med Hyg.* 60:238–243 (1999).

What is claimed is:

1. A compound of the formula

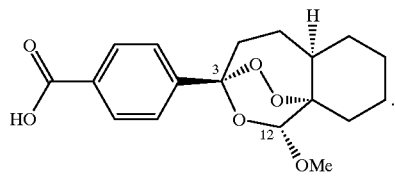

2. A compound of the formula

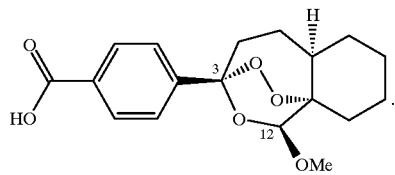

3. A method for treating malaria comprising the step of administering a compound according to claim 1 to an individual afflicted with malaria.

4. The method of claim 3 which further comprises administration of a second antimalarial compound.

5. The method of claim 4 wherein the second antimalarial compound is benflumetol.

6. A compound of the formula

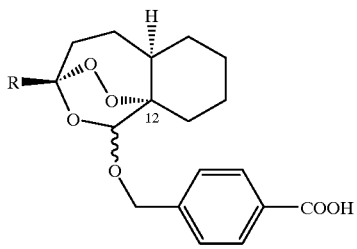

wherein R is selected from the group consisting of alkyl, alkenyl, aryl and heteroaryl.

7. The compound of claim 6 wherein R represents a p-fluorophenyl, p-carboxyphenyl, a p-$HO_3S$-phenyl, ethyl or a methyl group.

8. A method for treating malaria comprising the step of administering a compound of claim 6 to an individual afflicted with malaria.

9. The method of claim 8 which further comprises administration of a second antimalarial compound.

10. The method of claim 9 wherein the second antimalarial compound is benflumetol.

11. A method for treating malaria comprising the step of administering a compound according to claim 7 to an individual afflicted with malaria.

12. The method of claim 11 which further comprises administration of a second antimalarial compound.

13. The method of claim 12 wherein the second antimalarial compound is benflumetol.

14. A method for treating malaria comprising the step of administering a compound according to claim 2 to an individual afflicted with malaria.

15. The method of claim 14 which further comprises administration of a second antimalarial compound.

* * * * *